(12) United States Patent
Thimiri Govinda Raj et al.

(10) Patent No.: US 8,936,935 B2
(45) Date of Patent: Jan. 20, 2015

(54) PLASMA MEMBRANE ISOLATION

(75) Inventors: Deepak Balaji Thimiri Govinda Raj, Leuven (BE); Liesbet Lagae, Leuven (BE); Wim Annaert, Kontich (BE); Gustaaf Borghs, Leuven (BE)

(73) Assignees: IMEC, Leuven (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 546 days.

(21) Appl. No.: 13/111,428

(22) Filed: May 19, 2011

(65) Prior Publication Data
US 2011/0312056 A1  Dec. 22, 2011

(30) Foreign Application Priority Data
May 21, 2010  (EP) .................................. 10163644

(51) Int. Cl.
*B82Y 40/00* (2011.01)
*G01N 33/50* (2006.01)
*B82Y 5/00* (2011.01)
*G01N 33/68* (2006.01)

(52) U.S. Cl.
CPC .............. *G01N 33/5076* (2013.01); *B82Y 5/00* (2013.01); *G01N 33/6842* (2013.01); *Y10S 977/702* (2013.01); *Y10S 977/703* (2013.01); *Y10S 977/713* (2013.01); *Y10S 977/773* (2013.01); *Y10S 977/779* (2013.01); *Y10S 977/783* (2013.01); *Y10S 977/962* (2013.01)
USPC ...................... 435/317.1; 435/173.1; 977/702; 977/703; 977/713; 977/773; 977/779; 977/783; 977/962

(58) Field of Classification Search
None
See application file for complete search history.

(56) References Cited

U.S. PATENT DOCUMENTS

2004/0134565 A1  7/2004  Sun et al.
2006/0105049 A1*  5/2006  Fernandes et al. ............ 424/489

FOREIGN PATENT DOCUMENTS

WO  WO2009/126571  10/2009
WO  WO2010/008876  1/2010

OTHER PUBLICATIONS

Nitin, N. et al. Functionalization and peptide-based delivery of magnetic nanoparticles as an intracellular MRI contrast agent. J. Biol. Inorg. Chem. 2004. 9: 706-712.*
Lee, B et al. Polycefin, a new prototype of a multifunctional nanoconjugate based on poly(beta-L-malic acid) for drug delivery. Bioconjugate Chemistry. 2006. 17: 317-326.*
Knoll, W et al. Solid supported lipid membranes: New concepts for the biomimetic functionalization of solid surfaces. Biointerphases. Jun. 2008. 3(2): FA125-FA135.*
Spitz, DR et al. The effect of monosaturated and polyunsaturated fatty acids on oxygen toxicity in cultured cells. Pediatric Research. 1992. 32(3): 366-372.*
Xie, J et al. One-pot synthesis of monodisperse iron oxide nanoparticles for potential biomedical applications. Pure Appl. Chem. 2006. 78(5): 1003-1014.*
Chan, CP et al. Nanocrystal biolabels with releasable fluorophores for immunoassays. Analytical Chemistry. 2004. 76: 3638-3645.*
Raj, D.B. Thimiri Govinda Raj et al., "Cellular Uptake of Superpramagnetic Nanoparticles as a Strategy to Isolate and Characterize Endosomal Compartments", Frontiers Annual Meeting Leuven, Oct. 23, 2007, 1 page.
Arjunan, Selvam et al., "Limitations of the Colloidal Silica Method in Mapping the Endothelial Plasma Membrane Proteome of the Mouse Heart", Cell Biochem Biophys, vol. 53, 2009, pp. 135-143.
Dreger, Mathias, "Subcellular Proteomics", Mass. Spectrometry Reviews, vol. 22, No. 1, pp. 27-56, 2003.
Dubertret, Benoit et al., "In Vivo Imaging of Quantum Dots Encapsulated in Phospholpid Micelles", Science, vol. 298, Nov. 29, 2002, pp. 1759-1762.
Verma, Ayush et al., "Effect of Surface Properties on Nanoparticle-Cell Interactions", Small, vol. 6, No. 1, 2010, pp. 12-21.
Riviere, C. et al., "Internal Structure of Magnetic Endosomes", Eur. Phys. J. E, vol. 22, 2007, pp. 1-10.
Salgueirino-Maceira, Veronica et al., "Water-Based Ferrofluids from FexPt1-x Nanoparticles Synthesized in Organic Media", Langmuir, vol. 20, 2004, pp. 6946-6950.
Song, Ho-Taek et al., "Surface Modulation of Magnetic Nanocrystals in the Development of Highly Efficient Magnetic Resonance Probes for Intracellular Labeling", J. Am. Chem. Soc., vol. 127, 2005, pp. 9992-9993.
Spasic, Dragana et al., "Ref1p Competes With APH-1 for Binding to Nicastrin and Regulates y-secretase Complex Assembly in the Early Secretory Pathway", J. Cell. Biol., vol. 176, No. 5, Feb. 26, 2007, pp. 629-640.
Sun, Shouheng et al., "Size-Controlled Synthesis of Magnetite Nanoparticles", J. Am. Chem. Soc., vol. 124, 2002, pp. 8204-8205.
Laroy, Wouter et al., "Glycome Mapping on DNA Sequencing Equipment", Nature Protocols, vol. 1, No. 1, 2006, pp. 397-405.
Lee, Jae-Hyun et al., "Artificially Engineered Magnetic Nanoparticles for Ultra-Sensitive Molecular Imaging", Nature Medicine, vol. 13, No. 1, Jan. 2007, pp. 95-99.
Nel, Andre E. et al., "Understanding Biophysicochemical Interactions at the Nano-Bio Interface", Nature Materials, vol. 8, Jul. 2009, pp. 543-557.

(Continued)

*Primary Examiner* — Allison Fox
*Assistant Examiner* — Susan E Fernandez
(74) *Attorney, Agent, or Firm* — McDonnell Boehnen Hulbert & Berghoff LLP

(57) ABSTRACT

The present invention relates to a population of monodisperse magnetic nanoparticles with a diameter between 1 and 100 nm which are coated with a layer with hydrophilic end groups. Herein the layer with hydrophilic end groups comprises an inner layer of monosaturated and/or monounsaturated fatty acids bound to said nanoparticles and bound to said fatty acids, an outer layer of a phospholipid conjugated to a monomethoxy polyethyleneglycol (PEG) comprising a hydrophilic end group,
or comprises a covalently bound hydrophilic layer bound to said nanoparticles.

10 Claims, 19 Drawing Sheets

(56) References Cited

OTHER PUBLICATIONS

Peter, Jochen F. et al., "Enrichment and Detection of Molecules Secreted by Tumor Cells Using Magnetic Reversed-Phase Particles and LC-MALDI-TOF-MS", Journal of Biomolecular Technqiues, vol. 18, Issue 5, Dec. 2007, pp. 287-297.

Grimm, Marcus O.W. et al., "Regulation of Cholesterol and Sphingomyelin Metabolism by Amyloid-b and Presenilin", Nature Cell Biology, vol. 7, No. 11, Nov. 2005, pp. 1118-1123 and Supplemntary Information pp. 1-4 and p. 424.

Xiao, Zhan et al., "Identification of Detergent-Resistant Plasma Membrane Microdomains in Dictyostelium: Enrichment of Signal Transduction Proteins", Molecular Biology of the Cell, vol. 8, May 1997, pp. 855-869.

Blonder, Josip et al., "A Detergent- and Cyanogen Bromide-Free Method for Integral Membrane Proteomics: Application to Halobacterium Purple Membranes and the Human Epidermal Membrane Proteome", Proteomics, vol. 4, 2004, pp. 31-45.

Huh, Yun Suk et al., "Rapid Separation of Bacteriorhodopsin Using a Laminar-Flow Extraction System in a Microfluidic Device", Biomicrofluidics, vol. 4, 2010, pp. 014103-1-014103-10.

Tan, Feng et al., "Enrichment of Phophopeptides by $Fe^{3+}$-Immobilized Magnetic Nanoparticles for Phosphoproteome Analysis of the Plasma Membrane of Mouse Liver", Journal of Proteome Resarch, vol. 7, 2008, pp. 1078-1087.

Wilhelm, Claire et al., "Universal Cell Labelling With Anionic Magnetic Nanoparticles", Biomaterials, vol. 29, 2008, pp. 3161-3174.

European Search Report, European Patent Application No. 10163644.7 dated Apr. 12, 2011.

\* cited by examiner

SPMNPs        Membrane Staining        Merge

PLASMA MEMBRANE ISOLATION

FIELD OF THE INVENTION

The present invention relates to the manufacture and use of coated magnetic nanoparticles. More particularly the present invention relates to the use of these nanoparticles for the purification of plasma membranes and endosomes from cells. The present invention further relates to the analysis of the repertoire of proteins, lipids and carbohydrates which are present in the isolated plasma membranes and endosomes.

BACKGROUND OF THE INVENTION

Advances in protein separation technologies and innovations in MS (mass spectrometry) have greatly increased whole genome approaches in biology. However the explosion of information in the fields of genomics and proteomics has not been matched by a corresponding advancement of knowledge in the field of organellar proteomics, lipids and glycans, which is largely due to the structural complexity and the lack of powerful tools for their analysis. Hence, it has become more apparent that whole cells and tissues are not currently amenable to satisfactory whole "Omics" analysis. This is due to complexity and extreme dynamic range of protein expression in a whole cell (for example less abundant proteins are masked by those expressed at higher levels).

However, whole "Omics" analysis of subcellular compartments is hampered by difficulties inherent in purifying organelles as disclosed in Dreger (2003) *Mass Spectrom. Rev.* 22(1), 27-56. Particularly the analysis or proteins, lipids and carbohydrates in the plasma membrane and endosomal/lysosomal compartment system (EE/Lys) poses major hurdles as it is most dynamic in nature with strongly overlapping buoyant densities making it impossible to physically separate closely related populations. In addition, effective isolation and protein purification from subcellular compartments is the most crucial step for a whole genome analysis where only minute quantities are available. However, even the best optimized conventional purification methods such as density gradient centrifugation and colloidal silica based plasma membrane fractionation often lead to only partially purified compartments [Arjunan (2009) *Cell Biochem. Biophys.* 53(3), 135-143.].

Magnetic particles with targeting groups, such as antibodies have been used to isolate particular proteins or cells. Lipid coated magnetic particles have been used to deliver substances intracellularly. The use of such magnetic particles for the isolation of distinct cell membranes, such as e.g. plasma membrane and endosomes/lysosomes is unexplored. The present inventors disclosed the advantageous properties of a magnetic particle that would remain associated with a plasma membrane but are silent on the composition of beads that would have such properties [Nanotech Montreux meeting 17-19 Oct. 2008].

Other attempts to isolate plasma membrane derived endosomes are described in e.g. Rivière et al. (2007) *Eu. Phys J. E. soft matter* 22, 1-10 wherein magnetic particles are used which are not homogenous in size, resulting in an inefficient isolation process with low yield and purity and contamination with plasma membranes.

SUMMARY OF THE INVENTION

One aspect of the present invention relates to a population of monodisperse magnetic nanoparticles with a diameter between 1 and 100 nm which are coated with a layer with hydrophilic end groups. This layer with hydrophilic end groups comprises
a) an inner layer of monosaturated and/or monounsaturated fatty acids bound to the nanoparticles and bound to the fatty acids, an outer layer of a phospholipid conjugated to a monomethoxy polyethyleneglycol (PEG) comprising a hydrophilic end group,
or comprises
b) a covalently bound hydrophilic layer bound to the nanoparticles.

In particular embodiments the population according to claim 1 a), does not carry a peptide moiety such as membrane targeting peptides.

The nanoparticles can partially labelled with a detectable marker on the coating. In other particular embodiment the hydrophilic end group is selected from the group consisting of phosphonate, amine, $C_1$-$C_{20}$ alkane, $C_1$-$C_{20}$ alkene, $C_1$-$C_{20}$ alkyene, azido, epoxy, $NH_2$, COOH, unsubstituted or substituted PEG, PDP, CHO and SH.

In other particular embodiments, the phospholipids in the outer layer are selected from the group consisting of 1,2-Distearoyl-sn-glycero-3-phosphoethanolamine-N-[carboxy (polyethylene glycol)-2000](DSPE-PEGCOOH), 1,2-Distearoyl-sn-glycero-3-phosphoethanolamine-N-[amino (polyethylene glycol)-2000] (DSPE-PEG-Amine), 1,2-Distearoyl-sn-glycero-3-phosphoethanolamine-N-[methoxy (polyethylene glycol)-2000](DSPE-PEG), DSPEFolate, DSPE-PEG(2000) Maleimide and DSPE-PEG(2000) Carboxyfluroscein.

In particular embodiments, the covalently bound hydrophilic layer is selected from the group consisting of silane, dimercaptosuccinic acid (DMSA) and ammonium chloride. Optionally the silane is substituted with trimethoxy silyl, methoxyl silyl, ethoxy siliyl or silanol or the end group of the silane is substituted with a group selected from phosphonate, amine, thiol, $C_1$-$C_{20}$ alkyl, $C_1$-$C_{20}$ alkene, $C_1$-$C_{20}$ alkyne, azido and epoxy.

In other particular embodiments, the covalently bound hydrophilic layer which is bound to the nanoparticles is further modified with an endocytic pathway specific molecule wherein the pathways is selected from the group consisting of the clathrin-dependent, caveolae-dependent, ARF6-specific, clathrin-independent and caveolae-independent pathway.

The endocytic pathway specific molecule is selected from a peptide or protein (e.g. a receptor or receptor ligand, an antibody), a carbohydrate, a biotin, a virus and optionally further comprising a chromophoric molecule, for example a fluorescent label.

These endocytic pathway specific molecules can be conjugated to the nanoparticles via e.g. an amide, a disulfide or an ester bond.

Another aspect of the present of the invention is a method of preparing a monodisperse population of magnetic nanoparticles with a diameter between 1 and 100 nm which are coated with a layer with hydrophilic end groups, comprising the steps of:
a) providing a magnetic material,
b) applying a layer of monounsaturated and/or monosaturated fatty acid to the material by thermal decomposition under conditions to provide magnetic nanoparticles with a diameter between 1 and 100 nm,
c) precipitating the fatty acid coated magnetic nanoparticles with an alcohol,
d) discarding from the nanoparticles of step c) the population of aggregated nanoparticles and collecting the population of monodisperse nanoparticles, e) applying a layer of lipids comprising a hydrophilic end group to the monodisperse nanoparticles of step d).

f) selecting from the nanoparticles obtained in step e) the population of monodisperse nanoparticles in the presence of solvent, or instead of step e) and f), performing the step of g) replacing the fatty acid coating with a hydrophilic layer in the presence of a nonaqueous solvent (chloroform), h) selecting from the nanoparticles obtained in step g) the population of monodisperse nanoparticles in the presence of the non aqueous solvent.

Herein in step g, the layer with hydrophilic end group can be selected from the group consisting of DMSA, Silane, Tetramethylammonium hydroxide (TMAOH) and ammonium chloride.

In step g) the non aqueous solvent can be selected from the group consisting of organic-like alcohols, hydrocarbons and benzene derivatives.

in step g) the non aqueous solvent can be selected from the group consisting of toluene, cyclohexane, methanol, ethanol, mixtures of ethanol and toluene, chloroform, dimethylsulfoxide (DMSO) and dimethylformamide (DMF).

A further aspect of the invention relates to a monodisperse population of magnetic nanoparticles obtainable by the method described above.

A further aspect of the invention relates to an isolated complex of a nanoparticle with the plasma membrane or with a plasma membrane derived organelle such as an endosome.

A further aspect of the invention relates to the use of a population of nanoparticles as described or prepared above for the isolation of cell plasma membranes or for the isolation of endosomes.

Yet a further aspect of the invention relates to a method for isolating a plasma membrane of a cell, a fraction thereof, or a plasma membrane derived organelle, comprising the step of:
  a) providing a population of intact and suspended cells at a temperature where endocytic uptake by a cell is inhibited,
  b) contacting the intact cells with magnetic nanoparticles as described or prepared above, thereby allowing the binding of magnetic nanoparticles to and into the cell plasma membrane,
  c) removing unbound magnetic nanoparticles,
  d) disrupting the cells,
  e) removing cellular organelles,
  f) isolating from the disrupted cells by magnetic attraction the plasma membranes with magnetic nanoparticles.

An optional further step is the isolation of caveolae by treating the plasma membrane with mechanic shearing and detergents followed by a gradient separation.

A further optional step is the of isolating GPI anchored protein domains wherein plasma membranes or caveolae are treated with detergents and subjected to gradient separation.

In particular embodiments, in step e) the cell organelles are removed under conditions of 0, 1 to 2 M of salt concentrations and/or a pH between 10 and 12. A further aspect of the invention to plasma membranes obtained by the method described above, for the analysis of biological molecules comprised in the cell membranes. Typically these biological molecules are selected from proteins, carbohydrates and lipids. For example these proteins are an enzymatically active complex of gamma secretase.

A further aspect of the invention relates to a preparation of a plasma membrane, characterised in that at least 60% of the proteins in the preparation are integral membrane proteins or proteins associated therewith.

A further aspect of the invention relates to a method for isolating endosomes of a cell, comprising the step of:
  a) providing a population of intact cells at a temperature whereby endocytic mechanisms take place,
  b) contacting the intact cells for a period between 1 and 30 minutes at 37° C. with the nanoparticles described above, thereby allowing the uptake of nanoparticles into the endosomes.

This method further comprises the step of
  c) removing the unbound magnetic nanoparticles which have not been taken up by the cells,
  d) disrupting the cells and
  e) isolating by magnetic attraction endosomes with magnetic nanoparticles bound thereto from the disrupted cells.

Optionally the method further comprises after step b) the step of:
  maintaining the population of cells for a further period of between 1 and 180 minutes at a temperature whereby endocytic uptake by a cell takes place. A further aspect of the invention relates to the use of endosomes obtained by the method described above, for the analysis of a population of biological molecules comprised in the endosomes, such as proteins, carbohydrates or lipids. A particular example hereof is an enzymatically active complex of gamma secretase.

Isolation of subcellular organelles present an attractive target for whole proteomics, lipidomics and glycomics, as their proteins, lipids and glycans complexity is reduced and lower abundant ones that are specifically enriched on subcellular organelles compared to whole cell lysates could be identified. In addition subcellular approach is also advantageous in that identified proteins are linked to functional units. For novel proteins, the connection to an organelle can provide the first clues as to the protein functionality. Moreover, a global analysis on the organelle provides insights and understanding in the functional roles of the organelles.

The present invention discloses Magnetic NanoParticle (MNP)s-based methodologies for the isolation of plasma membrane and endosomes from control and disease-related cell lines and allows to analyze the proteome, glycome and lipidome content of such plasma membrane and endosomes. The invention allows to perform a comparative analysis supported by bioinformatics, and allows the identification of aberrant protein expression patterns from which potentially causal gene products and/or novel biomarkers may be identified.

The present invention relates to the development and characterization of biocompatible MNPs.

The present invention further allows to define parameters for cellular uptake and isolation of plasma membrane and endosomal compartments.

The present invention further provides an optimization of MNPs based plasma membrane isolation method for proteomics, glycomics and lipidomics.

Particular embodiments relate to the analysis of proteome, glycome and lipidome content of diseased cell lines or models of diseased cell lines, such as a Presenilins (PSEN)-deficient mouse embryonic fibroblast cell lines.

The invention relates to a method for synthesis of monodisperse and surface functionalized lipid coated MNPs for plasma membrane isolation. Herein an alcohol etching is performed and the lipid composition is adjusted for specific cell type plasma membrane isolation.

The invention relates to a method for synthesis of monodisperse and surface functionalized DMSA/Silane/TMAOH coated MNPs for endosomal isolation. Herein the surface composition is adjusted for specific endosomal compartmental isolation. Optionally an appropriate pathway-specific and application-specific bioconjugate is selected for endosomal specific targeting and isolation.

DETAILED DESCRIPTION OF THE INVENTION

Definitions

"Nanoparticle" (abbreviated as NP) in the context of the present invention refers to spherical particles with a diameter between 1 to 100 nm.

"Magnetic" material in the context of the present invention refers to magnetic (M), paramagnetic (PM) and superparamagnetic material (SPM).

"Monodisperse" in the context of the present invention related to nanoparticles which are homogeneous in nanoparticle shape and size. In the context of the present invention this refers to a population of nanoparticles wherein 90-95% of the nanoparticles fall within the defined size range.

"Plasma membrane" or "cell membrane" or "plasmalemma" refers to the lipid bilayer which surrounds the protoplasm of a cell. This membrane is not to be confused with the cell wall which covers plant and yeast cells.

"gamma secretase" refers to a protein complex comprising at least the proteins presenilin (PSEN1-NTF and PSEN1-CTF or PSEN2-NTF and PSEN2-CTF), nicastrin (NCT), APH-1 (anterior pharynx-defective 1) 1a (or APH-1b or APH-1c), and PEN-2 (presenilin enhancer 2).

A first aspect of the invention relates the modification of magnetic material. The magnetic material which is as such hydrophilic, is modified in order to obtain a hydrophilic outer layer which allows the nanoparticles to interact with and bind to the plasma membrane of a cell.

The present invention discloses two types of nanoparticles which have these advantageous properties.

The nanoparticles can be either magnetic paramagnetic or superparamagnetic. In a particular embodiment the nanoparticles are superparamagnetic.

The magnetic material can be any magnetic material known to the skilled person such as iron oxide, cobalt oxide, manganese oxide, nickel oxide zinc oxide or a combination of any of these materials.

A first type of nanoparticles relates to a population of monodisperse magnetic nanoparticles with a diameter between 1 and 100 nm which are coated with a hydrophobic layer with hydrophilic end groups. These nanoparticles contain an inner layer of monosaturated/mono-unsaturated/a combination of fatty acids bound to the nanoparticles. These mono-unsaturated fatty acids are selected from the group of myristoleic acid, palmitoleic acid, sapienic acid, oleic acid and erucic acid. The saturated fatty acids are selected from the group of lauric acid, myristic acid, palmitic acid, stearic acid, and arachidic acid.

Bound thereto is an outer layer of lipids comprising a hydrophilic end group. Suitable lipids in the context of the present invention comprise 1, 2-distearoyl-sn-glycero-3-phosphoethanolamine or other phospholipids conjugated to monomethoxy polyethyleneglycol (PEG).

These lipids are further substituted with a hydrophilic group such as NH2, COOH, unsubstituted or substituted PEG (polyethylene glycol), PDP (3-(2-pyridyldithio)propionate), —CHO (aldehyde group) or —SH (thiol group).

Particular embodiments of substituted liquids comprise 1,2 Distearoyl-sn-glycero-3-phosphoethanolamine-N-[carboxy (polyethyleneglycol)-2000] (DSPE-PEGCOOH), 1,2-Distearoyl-sn-glycero-3-phosphoethanolamine-N-[Amino (polyethylene glycol)-2000] (DSPE-PEG-Amine), 1,2-Distearoyl-sn-glycero-3-phosphoethanolamine-N-[methoxy (polyethylene glycol) -2000](DSPE-PEG), DSPE-Folate, DSPE-PEG(2000) Maleimide or DSPE-PEG(2000) Carboxyfluoroscein, and DSPE-PEG(2000) Biotin.

A second type of nanoparticles relates to a population of monodisperse magnetic nanoparticles with a diameter between 1 and 100 nm which have covalently bound thereto a hydrophilic layer.

Typically the same types of nanoparticles carrying a layer of fatty acids bound are used for the preparation. However instead of adding lipids to this layer, the layer is replaced by a hydrophilic layer. Suitable hydrophilic compounds for this layer are Silane, DMSA, and ammonium chloride.

The physicochemical properties of the nanoparticles determine the fusion with the plasma membrane of a cell.

One property is the size of the nanoparticles, which is between 1 and 100 nm. In preferred embodiments the monodisperse population of nanoparticles has a diameter around 10 nm (between 5 and 15 nm or between 8 and 12 nm). In embodiments where nanoparticles are targeted and internalised via phagocytosis nanoparticles with a diameter between 60 and 100 nm are envisaged.

The other properties of the nanoparticles are the hydrophilic and charge nature of the nanoparticles which can be measured by determining the zeta potential of the nanoparticles. In order to achieve a maximal uptake by a plasma membrane the zeta potential of the nanoparticles is measured and the composition of the coating is accordingly measured.

Zeta potential has been used to detect the cellular interaction with charged nanoparticles and in general negatively charged nanoparticle will decrease the surface Zeta potential and positively charged nanoparticle will increase the surface Zeta potential. These interaction effects can be observed with the changes in the zeta potential values are relative to cell surface charge and nanoparticle surface charge. Firstly, the binding of the nanoparticles to the plasma membrane will change the zeta potential value of the cells. During endocytosis, cells take up external materials by invaginating a small portion of the cell surface plasma membrane to form a new intracellular vesicle around the substance to transport inside the cells. Since the cell membrane is overall negatively charged, the loss of negatively charged cell membrane during vesicular transport and charged nanoparticles loaded inside the vesicles will cause the zeta potential values to become to less negative. Hence in order to use the nanoparticle for cell surface plasma membrane isolation or for endosomal compartmental isolation, nanoparticle's surface composition should be optimized depending on the zeta potential of the cell surface and culture medium. This allows the skilled person to design and select for any type of cell the appropriate type of nanoparticles which can fuse with the plasma membrane or which can be internalised in the endosomes. For example if if the cell type has a zeta potential of −31.16 mV at pH7, positively charged nanoparticles ($NH_2$-lipid end group nanoparticles) which has a zeta potential in the range of 10-30 mV at pH 7.

The nanoparticles and methods of the present invention allow to isolate plasma membranes of any eukaryotic cell type, including fungi, yeasts, plants, and animals such as mammals. The properties of the plasma membrane are highly similar, allowing to application of the technology to any eukaryotic cell, when the eventual cell wall covering the plasma membrane is removed or disrupted.

The size and physicochemical nature of the nanoparticles allow the fusion with the plasma membrane and/or the uptake by the endosomes without the additional presence of a targeting element such as an antibody, ligand, receptor, for a plasma membrane specific protein.

However for the targeting of specific subpopulations of endosomes, nanoparticles which have a covalently bound hydrophilic layer bound to the nanoparticles can be further modified with antibodies, ligands of receptors, receptors, carbohydrates and other compounds which provide specific targeting to a subpopulation of endosomes.

Optionally magnetic nanoparticles can be further labelled with a detectable marker, such as radioactive magnetic metal or radioactive or isotope labelling of the layer around the magnetic material. Alternatively, a part of the layer is functionalised with a fluorescent, or other chromophoric group.

The present invention demonstrates that the efficiency of the labelling of plasma membranes and/or endosomes is influenced by the size distribution of the nanoparticles and the efficiency of coating the nanoparticles with the fatty acid layer. These advantageous properties are obtained by manufacturing of the nanoparticles using the methods as disclosed in the present invention.

In the methods of the present invention magnetic nanoparticles are manufactured by a thermal decomposition method as published in Sun and Zeng (2002) *J. Am. Chem. Soc.* 124(28), 8204-8205 or in US20040134565. This method has the advantage that nanoparticles with a controlled size are obtained. Briefly a mixture of a metal acetylacetone, 1,2-RCH(OH)CH$_2$OH+RCOOH+RNH$_2$ is heated at prolonged time. Herein the metal can be any of Fe, Co, Mn, NI, Zn or a combination thereof and R is $C_{12}$ to $O_{24}$. The reaction temperature and time can be adjusted to obtain a population of magnetic nanoparticles of desired diameter. Although different methods have been used to generate magnetic nanoparticles for biological imaging and cell and/or organelle targeting, the importance of the homogeneity of the nanoparticle size population has been underestimated for the targeting of nanoparticle to plasma membranes. Only nanoparticles with a well defined size will fuse with the membrane. Larger nanoparticle, will not interact with the membrane or will bind aspecifically and temporarily to the membrane, as has been documented for e.g. cationic silica beads. Smaller nanoparticles will be taken up by the cell at an unwanted rate or via an unwanted mechanism. Such nanoparticles will end up in organelles or in the cytoplasm. Upon disruption of cell, the cellular material which will be purified with magnetic nanoparticles will consequently be contaminated with intracellular material. Until present the use of magnetic nanoparticles which are prepared with a thermal decomposition method for the binding to plasma membranes has been unexplored.

In the prior art methods, the use of an organic coating, such as oleic acid, to prevent agglomeration is described in US20040134565. However the nanoparticles described therein are used in the production of larger structures wherein the nanoparticles are compacted or compressed.

For the purpose of the present invention it has been found that the method of isolating the nanoparticles from the reaction mixture has a significant effect on further applications wherein the nanoparticles are used for binding to plasma membranes.

It has been found that due to the organic coating, such as oleic acid, the coated nanoparticles can be precipitated with an alcohol such as methanol, ethanol, propanol, butanol or mixtures thereof, whereby the unreacted magnetic material remains in solution. On the other hand it was found that under conditions whereby e.g. more than 75% (V/V) of ethanol is used, a part, or all, of the organic coating is removed from the magnetic nanoparticles.

Under the appropriate conditions, the precipitation step as explained above generated magnetic nanoparticles which have a homogeneous coating. This has the advantage that the physicochemical character of the coating and the modifications thereof will be equally of an unexpected homogeneity.

In summary, the homogenous size and homogeneous coating of nanoparticles which are prepared as explained above provides a population of nanoparticles which will also behave more homogeneously and predictable when these nanoparticles are contacted with cells.

The coated nanoparticles as obtained by the thermal decomposition methods are further modified by two alternative methods. In a first method the coating is further modified. In a second method the coating is replaced.

In the method wherein the coating is modified the coated nanoparticles are mixed with one or more phospholipids in the presence of an organic solvent such as chloroform to obtain block-copolymer micelles following a procedure as published by Dubertret (2002) *Science* 298(5599), 1759-1762. Prior to the ligand addition step the nanoparticles are precipitated with an alcohol (less than 75% v/v).

In the method wherein the coating is replaced a ligand exchange method is used. Briefly. nanoparticles were dispersed in an organic solvent and then DMSA, Silane, or TMAOH is added dissolved in an alcohol or solvent such as chloroform or DMSO following a procedure as published by Lee et al (2207) *Nat Med* 13(1), 95-99; Salgueirino-Maceira et al. (2004) *Langmuir* 20(16) 6946-6950 and Song et al. (2005) *J. Am. Chem. Soc.* 127(28), 9992-9993. For effective ligand exchange method, complete surface etching is performed using 75% v/v) alcohol precipitation step.

Whereas other methods such as chemical co-precipitation also lead to nanoparticles which are functionalised with the same functional groups, these methods inherently lead to a less homogeneous population in size and coating and make the less suitable for the specific targeting to plasma membrane.

The magnetic nanoparticles of the present invention make it possible to isolate plasma membranes and endosomes with a yield and purity which is superior over prior methods. In addition methods as described in the present invention require less steps than prior art methods, and result in plasma membranes and/or endosomes wherein the proteins or protein complexes have an activity which is significantly higher, or results even in isolated proteins which previously could not be isolated without loss of activity.

Accordingly one aspect of the present invention relates to a method for the isolation of a plasma membrane of a cell, a fraction thereof, or a plasma membrane derived organelle, comprising the following steps:

A population of intact and suspended cells is provided at a temperature where endocytic uptake by a cell is inhibited, e.g. below 25° C., below 18° C., below 12° C., between 2 and 6° C. (such as at about 4° C.).

The intact cells are contacted with magnetic nanoparticles as described above. The physicochemical parameters (size of the nanoparticle and hydrophobic nature or the coating) allow the binding of these magnetic nanoparticles to and into the plasma membrane. The defined size distribution and low temperature allows targeting the plasma membrane with only a negligible uptake into other cell organelles.

Unbound magnetic nanoparticles are removed by one or more washing steps, in a buffer which preserves the integrity of the cells.

Thereafter the cells are disrupted, by e.g. osmotic shock or mechanical sheering (typically using a ball-bearing cell cracker) and organelles such as nuclei are removed by centrifugation.

The fraction of the disrupted cells which comprises magnetic nanoparticles is isolated using magnetic purification methods, typically with a magnetic force in the range of 0.1-0.5 Tesla magnetic. In particular embodiments the fraction of the disrupted cells which comprises magnetic nanoparticles is bound on a column of ferromagnetic beads in the presence of a magnetic field, allowing to further wash to bound fraction or to perform additional manipulations on the bound fraction.

Alternatively or in addition, contaminating cell organelles are washed out under high salt condition (between 0, 1 and 2 M salt) and/or in the presence of alkaline buffers with a pH between 10 and 12.

The methods as described above allow the isolation of plasma membranes which have a significant higher degree of purity than prior preparations, as illustrated in the accompanying experimental data.

In addition to the above described general method, fractions of plasma membranes can be equally isolated.

For example, isolated plasma membranes can be further treated by mechanical shearing and the addition of detergents to release cholesterol-rich microdomains or caveolae from the plasma membrane. The caveolae are separated from the plasma membrane by a gradient separation.

Another aspect of the present invention relates to the isolation of endosomes from a cell population. These methods comprise the following steps:

A population of intact and viable cells is provided and maintained a temperature where endocytic mechanisms take place, generally above 25° C., typically at about 37° C.

These cells are then contacted for a predetermined period (typically between 1 and 30 minutes with magnetic nanoparticles, which are taken up by the cells into the endosomes. (this step is also described as the "pulse")

Optionally, the above "pulse" step is followed by a so-called "chase" step whereby the unbound magnetic nanoparticles are removed, and whereafter the cells are further incubated at temperature where endocytic mechanisms take place for a period which may range from about 1 to 180 min. During this chase step, magnetic nanoparticles will be further sorted from the plasma membrane into the endosomes.

Hereafter the cells are also disrupted whereafter the endosomal fraction is removed from the lysate by magnetic attraction.

The methods of the present invention provide a number of unprecedented advantages as indicated in table 1. Due to their small size (<100 nm) the magnetic nanoparticle, do not interfere with mass spectrometry methods and behave as a salt, and this in contrast with silica beads. The absence of detergents in the isolation method for plasma membranes preserves the structure and function of proteins, carbohydrates and lipids.

TABLE 1 comparison of various plasma membrane isolation techniques

| Properties | Silica Bead | Density Gradient | Antibody conjugated Microbeads | Magnetic nanoparticles of present invention |
|---|---|---|---|---|
| Cell type specific | Universal | Universal | Antibody specific | Universal |
| Yield | Low yield | Low Yield | Yield depends affinity | High Yield |
| Process | One-Step | Multiple step | Multiple steps | One-step |
| Purity | Low Purity | Low purity | High Purity | High resolution |
| Proteomics | good | good | good | Good |
| Lipidomics | None | none | None | Good |

TABLE 1-continued comparison of various plasma membrane isolation techniques

| Properties | Silica Bead | Density Gradient | Antibody conjugated Microbeads | Magnetic nanoparticles of present invention |
|---|---|---|---|---|
| Glycomics | None | None | None | Good |
| Enzyme Activity | none | None | none | Good |

EXAMPLES

Example 1

Synthesis of Superparamagnetic $Fe_3O_4$ Nanoparticles (SPMNPs)

$Fe_3O_4$ nanoparticles were synthesized using thermal decomposition method as reported by Sun (cited before). In a typical synthesis for 8 nm $Fe_3O_4$ nanoparticles, Iron (III) acetylacetonate (2 mmol), 1,2-hexadecanediol (10 mmol), oleic acid (6 mmol), oleyl amine (6 mmol) and benzyl ether (20 ml) were mixed and magnetically stirring the under $N_2$ flow conditions. The mixture was heated to 200° C. for 2 hours and then refluxed at 300° C. for 1 hour. The black colored mixture was cooled to room temperature by removing the heat source. Further black material (SPMNPs with oleic acid layer as shell coating) was precipitated by adding ethanol at appropriate percentage depending on the further functionalization step and was magnetically separated using a rare earth magnet. Finally, SPMNPs were dispersed in hexane and centrifuged step (5000 rpm, 10 minutes) was performed to remove aggregates.

These $Fe_3O_4$ nanoparticles were coated with DSPE (2000) phospholipids by adopting the ligand addition procedure described for water soluble quantum dots (Dubertret cited before).

In a typical experiment, 5 mg of SPMNPs were dissolved in 1 ml of chloroform. DSPE (2000)-PEG-$NH_2$ (10 mg) was added to the solution and vortexed for 4 hours followed by the removal of chloroform by evaporation. The residual solid was dried by $N_2$ flow for 5 minutes, and 1 ml of deionized water was added immediately. After 5 minutes of vigorous stirring, a uniform transparent water soluble SPMNPs aqueous solution was formed. Further centrifugation for 10 minutes at 5000 rpm was performed in order to remove the aggregates. The supernatant was further purified by running through Miltenyi MACS LS column in the presence of magnetic field. Finally the bound fraction (lipid coated SPMNPs) were resuspended in 1 ml of PBS solution. Further the SPMNPs concentration and size were determined using TGA and DLS respectively.

To increase the cationic property of SPMNPs and for enhanced electrostatic interaction with cells, the stoichiometric ratio between SPMNPs and DSPE phospholipids can be adjusted.

For example: For MEFs wild-type, 1:1 ratio of SPMNPs (5 mg) and DSPE phospholipids (5 mg) were used for functionalization. While for MEFs PSDKO, 1:2 ratio of SPMNPs (5 mg) and DSPE phospholipids (10 mg) were used for lipid functionalization. The ideal stoichiometric ratio for maximum plasma membrane sheet isolation can be determined by setting pilot experiments wherein different ratios are tested. To generate fluorescently labeled SPMNPs, 1:4 compositions (CF (fluorescent label) versus $NH_2$ substituted phospholipds) were used in the functionalization step.

DMSA (dimercaptosuccinic acid), TMAOH (Tetramethylammonium hydroxide), COOH-TMACl ((3-carboxylpropyl) trimethylammonium chloride) coated SPMNPs were synthesized by ligand exchange methodology as cited above in [Lee (2007) Salgueirino-Maceira, et al. (2004) and Song et al. (2005). After the reaction, SPMNPs were dissolved in water, magnetic purified and then adjusted the pH of the solution to be 7. (FIG. 1)

Several techniques were applied to the SPMNPs as a quality control.

Transmission EM. SPMNP suspensions were adhered onto a carbon-coated copper grid, dried and imaged on a 300 kV Philips CM30 instrument equipped with a field emission gun electron source.

Thermal gravimetric analysis (TGA). SPMNP concentration measurements were performed on a TA instruments Q5000 IR under $N_2$ atmosphere.

Dynamic light scattering (DLS) and Zeta potential measurement. The hydrodynamic diameters and zeta potential measurement of SPMNPs were measured using Zetasizer Nano-ZS DLS system (Malvern Instruments Ltd., England) and reported as number average using DTS application software Magnetic Characterization of SPMNPs.

Magnetization measurements were made using a standard alternating gradient field magnetometer (AGFM Model 2900, Princeton Instruments NJ).

Stability in SPMNPs. Stability of SPMNPs in medium/$H_2O$ was performed using UV-vis spectroscopy conducted on a Shimadzu UV-1601 PC spectrophotometer and recorded between 300 and 1000 nm with a 0.5 nm resolution.

Example 2

Development and Functionalization of SPMNPs for Subcellular Compartmental Isolation SPMNPs are inorganic nanocrystals characterized by superparamagnetic and size controlled physical properties which can be fine-tuned depending on the application of interest. In particular for subcellular isolation, nanoparticle-cell surface interaction is the critical step and mainly governed by three major physiochemical properties such as size, shape and surface coating [Nel et al., (2009) *Nat Mater* 8, 543-557; Verma & Stellacci (2010), *Small*. 6(1), 12-21]. Hence, the effect of surface coating dependent selection of SPMNPs for subcellular localization and magnetic isolation was investigated. Herein SPMNPs with a 10 nm diameter have been synthesized by the thermal decomposition method generating monocrystalline $Fe_3O_4$ with narrow size distribution and high magnetization value (~60 emu/g). However these SPMNPs were hydrophobic due to oleic acid coating and were further functionalized using two alternative methodologies:

a) Ligand exchange: DMSA/TMAOH/COO-TriMACl, or
b) Ligand addition: DSPE-Lipids. Functionalized SPMNPs were characterized for their physical properties showing retention of superparamagnetism and slight increase in size.

Example 3

SPMNPs-Cell Interaction and Magnetic Cell Isolation

HeLa and MEFs (wild-type) were grown to 70% confluence in 4 plates with a diameter of 10 cm dish plates. Initially cells were washed three times with PBS (37° C.) and incubated with SPMNPs in DMEM/F12 medium for various time periods and at increasing nanoparticle concentration. After incubation, cells were trypsinized and harvested by centrifugation at 1000 rpm for 10 minutes. Further cell viability analysis was performed using trypan blue staining and magnetic cell isolation using SuperMACSII magnetic separation system.

MEFs (WT, PSENDKO, PSEN1r) cells grown to confluence in 8 plates with a diameter of 10 cm, were initially incubated in ice cold DMEM for 30 minutes at 4° C., washed three times with ice cold phosphate buffered saline (PBS) and then incubated with SPMNPs in PBS (2 mg/ml) for 20 minutes at 4° C. with slow horizontal shaking. After the incubation, cells were harvested in PBS, centrifuged (1000 rpm, 10 minutes) and homogenized in homogenizing buffer HB (250 mM sucrose, 10 mM Hepes and 1 mM EDTA pH 7.4 supplemented with protease inhibitors) using a ball-bearing cell cracker (20 passages, clearance 10 µm, Isobiotec, Germany). After low-speed centrifugation (200 g, 10 minutes), the post nuclear supernatant (PNS) were loaded on to equilibrated LS column in presence of SuperMACSII magnetic system (Miltenyi Biotec), extensively washed sequentially with ice-cold HB, high salt 1M KCl and high pH 0.1 M $Na_2CO_3$ respectively, and the purified plasma membrane fraction was eluted by removal from the magnet. The plasma membrane fraction was enriched by ultracentrifugation (55,000 rpm, 1 hour) and resuspended in 200 µl HB buffer for further analysis. For western blot and total protein analysis, samples concentration were determined using a Bradford assay (Bio-Rad) and protein separation were run in NUPAGE Novex pre-cast 4-12% gradient Bis-Tris gel (Invitrogen). Further processing was performed using ECL detection protocol (Western Lightning, PerkinElmer).

Of the different types of nanoparticles DMSA and Lipid-SPMNPs showed medium stability and hence were used for cellular (HeLa and MEFs) viability and uptake. No detectable cell death was detected with trypan blue staining after 2 hours of SPMNPs incubation. A surface coating-dependent variation in cellular uptake of SPMNPs was observed with the following trend in magnetic cell isolation ($NH_2$-lipid>DMSA>PEG-lipid>COOH-lipid-SPMNPs, whereby $NH_2$-lipid coated SPMNPs have the highest cellular uptake).

Further experiments on surface coating based selection were performed with $NH_2$-lipid/DMSA coated SPMNPs for Pulse-Chase labeling and subcellular compartmental isolation without the use of any biomolecule (i.e. targeting moieties such as antibodies, peptides, ligand, etc).

Using DMSA/lipid-SPMNPs, the Pulse-Chase methodology for magnetic endosome isolation was optimized based on concentration, chase time and by studying the level of subcellular compartment proteins in the magnetic fraction (MF) using western blot (WB) analysis.

Depending on the chase period, MFs from DMSA-SPMNPs were enriched either in early endosomal marker EEA1 (15-30 minutes), or the late endosomal marker Rab7 (60 minutes). However MF from lipid-SPMNPs ($NH_2$ endgroup) showed enrichment in the plasma membrane marker $Na^+K^+$ ATPase for all Pulse-Chase conditions. Based on these results, $NH_2$-lipid-SPMNPs and DMSA-SPMNPs were selected for plasma membrane and endosomal isolation respectively.

Example 4

Isolation of Endosomal Fraction

90% confluent HeLa cells grown on 10-cm dishes were incubated for 15 minutes at 37° C. with SPMNPs [DMSA] in medium (200 µg/ml). Then they were washed in PBS and chased at 37° C. for various time periods. Cells were washed and harvested in PBS, centrifuged and homogenized in homogenizing buffer HB using a ball-bearing cell cracker. After low-speed centrifugation (400 g, 10 minutes), the Post Nuclear Supernatant (PNS) were loaded in SuperMACSII magnetic system, washed with ice-cold HB and the concentrated magnetic fraction was resuspended in HB buffer. The magnetic fraction (MF) was pelleted by ultracentrifugation (55,000 rpm for 1 hour) and resuspended in 200 µl HB buffer for further western blot analysis.

Example 5

Analysis of Plasma Membrane Proteomics Glycoproteomics and Lipids

Lipid Extraction and ESI-MS/MS Based Analysis.

A qualitative and quantitative Proteomics, Glycomics and Lipidomics analysis was performed between the wild type, PSENDKO [Presenilin 1 and 2 double knock out] and PSEN1r [Presenilin rescued with human PSEN1] MEF.

Peter et al. (2007). *J Biomol Tech.* 18(5), 287-297 described a magnetic carrier based methods for plasma membrane membrane isolation. These magnetic purification procedures require additional detergent/acid wash steps to release proteins from the magnetic beads for suitable MS analysis.

The nanoparticles as used in the present invention have a very high surface to volume ratio and small size. These nanoparticles do not interfere with MS analysis and provide a clear enrichment for plasma membrane (protein, lipids and glycans) compared to the total fraction. Accordingly the present invention allows to perform a novel detergent-free plasma membrane isolation method which is compatible with MS analysis compared to existing antibody/detergent based magnetic purification methods.

Proteomics

For separation of N-terminal peptides by COFRADIC, cell membrane fraction were lysed, disulfide bonds were reduced and alkylated prior to acetylation of N-termini with trideutero-acetyl N-Hydroxy-Succinimide. Samples were digested with trypsin, V8 protease or chymotrypsin overnight at 25° C. or 37° C., respectively. Purified dried peptides were reconstituted in 0.1% trifluoroacetic acid (TFA) and separated on an Ultimate 3000 LC system. During the primary run, 16 fractions of 4 minutes each were collected and dried under vacuum. N-termini of internal peptides were derivatized with TNBS. Afterwards, fractions were applied to a secondary RP-HPLC run with identical chromatographic conditions. Fractions were collected in the same time intervals as before, dried under vacuum and prepared for LC-MS/MS analysis. The quantitative differential aspect of the procedure was also performed by reacting peptides with propionylC$^{13}$-sulfo NHS (heavy) and propionylC$^{12}$-sulfo NHS (light). Two such experiments were performed comparing wild-type and PS−/− MEFS with heavy and light labels switched for the repeat experiments.

Proteomics analysis of plasma membrane fractions showed clear enrichments for integral membrane proteins (70%) compared to the PNS fraction. Fragmented peptide spectra were identified using Mascot search algorithm and identified approximately 2000 unique proteins in the plasma membrane fraction. Similar trends were observed with respect to PSENDKO and PSEN1r samples. This degree of purity is substantially higher compared to existing technologies such as cell surface biotinylation, density gradient centrifugation and antibody based magnetic purification. Furthermore and using Gene Ontology (GO) based database analysis, 150 unique proteins were observed which are present only in the wildtype plasma membrane and 300 unique proteins which are present only in the PSENDKO plasma membrane fraction. Significantly more cell migration related proteins are represented in the wildtype plasma membrane proteome (Wildtype—6%, PSENDKO—1%), while adhesion related proteins are more present in the PSENDKO plasma membrane fraction (Wildtype-6%, PSENDKO-8%). These results were confirmed using cell migration assays and confocal analysis on the indicated cell lines.

ICAT labeling based differential proteomics observed the absence of certain proteins in PSDKO and a, increase of certain proteins in the wildtype MEFs (about 80 proteins).

Lipidomics

Cell membrane was isolated using lipid coated SPMNPs as stated previously. To prepare lipid extracts for ESI-MS/MS analysis, the cell membrane fraction and Post Nuclear Supernatant (PNS) were mixed with 0.9 ml of 1N HCl: Methanol 1:8 (v/v). CHCl$_3$ (0.8 ml) and 200 µg/ml of the anti-oxidant 2,6-di-tert-butyl-4-methylphenol (Sigma) were added. After addition of the lipid standards, the organic fractions were collected by centrifugation at 200 g for 5 minutes. Samples were evaporated and reconstituted in CH$_3$OH:CHCl$_3$: NH$_4$OH (90:10:1.25, v/v/v) and the lipids were analyzed by electrospray ionization tandem mass spectrometry (ESI-MS/MS) on a hybrid quadrupole linear ion trap mass spectrometer (4000 QTRAP system; Applied Biosystems, Foster City, Calif.) equipped with a robotic nanoflow/ion source (Advion Biosciences). The system was operated in the MRM mode for quantification of individual species. Data were expressed as fold change relative to the control samples (wild-type) and were presented as heatmaps using the Heatmap Builder software (Clifton Watt, Stanford University, USA).

Cholesterol and Total Spingomyleinase Activity Determination

Cholesterol levels were determined using the Amplex-Red cholesterol assay (Molecular Probes). Similarly Spingomyleinase activity was measured using the Amplex-Red Sphingomyelinase Assay Kit (Molecular Probes). Total SM concentrations were determined enzymatically using a modified assay from the Amplex-Red Sphingomyelinase Assay Kit (Molecular Probes). Briefly, for SM determination, membrane fraction was adjusted to a protein concentration of 0.15 mg/ml using a bicinchoninic acid assay. A 100 µl sample was added to a 100 µl assay solution, which contains 100 µM Amplex Red reagent, 2 U ml-1 HRP, 0.2 U ml-1 choline oxidase, 8 U ml-1 of alkaline phosphatase, 1 mU nSMase and 0.1 M Tris-HCl, 10 mM MgCl$_2$, pH 7.4. After preincubation for 1 h at 37° C. under light exclusion conditions, fluorescence was measured for 30 minutes using excitation at 530±2.5 nm and fluorescence detection at 590±2.5 nm. The slope, which has to be 0, was calculated to scrutinize the completeness of the reaction. The values were corrected from the background signal that was determined by samples treated in the same way as described above but which did not contain any SMs.

A lipid profiling on total and plasma membrane fractions in WT and PSENDKO MEFs was performed for the following lipids: Cholesterol (Choi), Phosphatidylcholine (PC), Phosphatidylserine (PS), Phosphatidylethanolamine (PE), Phosphatidylinositol (PI) and Sphingomylein (SM) lipids using ESI/MS analysis. We observed clear enrichments at the plasma membrane and deciphered the hallmarks of plasma membrane lipid composition including an increase in SM (8% increase) and decrease in PI (4% descrease) with respect to the PNS. Furthermore we performed quantitative and qualitative comparisons of plasma membrane lipid level vs. total between WT and PSENDKO plasma membrane fractions. In these analyses, we observed significant increase in SM and Chol levels in PSENDKO PNS fractions compared to the wildtype levels as published in Grimm (2005) *Nat. Cell Biol.* 7(11), 1118-1123. In addition, we also identified a reverse trend, i.e. decrease in Chol level, at the plasma membrane of PSENDKO MEFs. This was next confirmed using filipin staining and confocal analysis demonstrating clear intracellular enrichments for Chol while less staining was observed at the cell surface. With respect to the other phoshopholipids PC, PS and PI, there was no significant difference between the wildtype and PSENDKO in terms of lipid levels. At the same time, we identified variations between the lipid species in the PC and SM families. For example SM species (16:1, 18:0 & 18:1) were significantly higher in PSENDKO PNS fraction compared to wildtype, while there was no significant variation in the plasma membrane fraction. In addition we observed increased levels of unsaturated PC species at plasma membrane and similar trends for PI, PS, and PE with respect to PNS and plasma membrane for PSDKO vs. wildtype. Currently we are comparing the lipid profiles with the one of the PSEN1 rescued MEFs (PSEN1r) to validate our analysis. With respect to cholesterol levels, no significant difference between the wildtype and PSEN1r (PM, PNS) was observed thereby showing recovery in cholesterol trafficking. Further differential lipid profiling will be performed in order to generate complete lipidomics on PSEN1r and also to further scrutinize our methodology.

Glycomics

N-termini of internal peptides fractions were pooled as stated previously. Prior to an identical secondary RP-HPLC separation, each pooled fraction was redissolved in 85 µl of a freshly prepared 50 mM ammonium bicarbonate buffer (pH 7.8), and 0.8 units of peptide N-glycosidase (PNGase F) from Chryseobacterium (Flavobacterium) meningsepticum (proteomics grade, g95%, Sigma-Aldrich) was added. Hydrolysis of N-linked sugar chains from peptide backbone asparagines was allowed for 20 minutes at 30° C. The reaction was stopped by adding 10 µl of 50% acetic acid. Each PNGase F treated pool of primary fractions was loaded onto the same RP-HPLC column and the same solvent gradient was applied as during the primary separation. The altered peptides were collected in secondary fractions, dried under vacuum and prepared for LC-MS/MS analysis.

Based on the identified sites and using GO databases, we could identify the proteins and locate known N-glycosylation sites (For example: Nicastrin potential N-glycosylation site at $44^{th}$ amino acid was identified). Based on the MS and database analysis, 235 glycosylated proteins were identified in which 65 are known and 100 are potential sites, respectively. Next, we demonstrate that the SPMNPs-based plasma membrane extraction can be interfaced with downstream Fluorophore Assisted Carbohydrate Electrophoresis as published in Laroy et al. (2006) *Nat. Protoc.* 1(1), 397-405, resulting in glycan profiling. Using this approach, we observed significantly higher N-glycan sialylation levels in PSENDKO compared to wildtype plasma membrane fractions. This difference could not be clearly observed when analyzing PNS, likely due to the high content of immature N-glycans in the spectra. Further structural analysis confirms that structures are typical bi- and tri-antennary. We also confirmed the absence glycans originating from any serum related protein which in general is a limiting factor for cell surface glycomics. Currently we are studying whether there is any recovery in N-glycan sialylation level in the PSEN1r plasma membrane fraction similar to the WT.

Example 6

Isolation of Active Protein Complexes from Cell Membrane

Cell membrane was isolated using lipid coated SPMNPs as stated previously. To prepare microsomal membranes from the cell membrane, pelleted magnetic fraction was resuspended in PIPES buffer (20 mM PIPES pH7, 140 mM KCl, 0.25M Sucrose, 5 mM EGTA, Protease inhibitor) containing 1% CHAPS (sigma-Aldrich) and solubilized for 1 hour at 4° C. Following sequential ultracentrifugation for 30 minutes and 15 minutes (100,000 g 4° C.) the cleared supernatant was collected. Similarly, microsomal membranes were isolated from the PNS and further obtained supernatants (from PNS & Bound) were used for cell free enzyme activity studies.

Example 7

Development of a Cell Free Gamma-Secretase Assay

PM and PNS fractions were extracted in CHAPS and mixed with recombinant APP-C99-FLAG affinity isolated from transiently transfected Aph1$^{-/-}$-MEFs as described in Spasic et al. (2007) *J Cell Biol* 176(5), 629-640. Newly produced APP intracellular domain (AICD) was separated on 10% precasted gels (NuPAGE) in MES buffer and analyzed for Western blotting.

The formation and levels of γ-secretase complexes at the PM, protein complexes were extracted from microsomal membranes from PNS and plasma membrane with 0.5% dodecylmaltoside (DDM) and were run on a Native gel.

The novel technology of the present invention was compared it with established methods like cell surface biotinylation (CSB) to study the levels of gamma-secretase components like Nicastrin (Nct), Presenilin 1 & 2 (PS1&2), Anterior pharynx defective-1 (APH1a) and Presenilin enhancer-2 (PEN2) at the cell surface. All methods (including confocal analysis of isolated plasma membrane sheets) confirmed the higher abundancies of PS1, NCT, PEN2 and APH1a at the cell surface while much lower levels (about 1-2%) for PSEN2 were measured. Next we quantified the levels of intact gamma-secretase complexes as well as activity in i SPMNP isolated PMs using blue native electrophoresis (complexes) as well as a cell free gamma-secretase assay. These data directly establish that most if not all components exist in active gamma-secretase complexes at the PM. Moreover, we also observed a significant enrichment in terms of quantity and quality of gamma-secretase complexes when comparing plasma membrane fractions with PNS. In summary the present inventions provides an SPMNPs based plasma membrane method, which is detergent-free and does not rely on IP (Immune precipitations) for the isolation of pure and biological active PMs including active gamma-secretase complexes. These data are part of a larger project and paper studying the distinct distribution of PSEN1 and PSNE2-containing complexes in the endocytic pathway and cell surface.

Example 8

Validation of Results Based on Fluorescent Labeled SPMNPs

Transmission EM. After magnetic labeling, cells were washed twice with PBS–/– and sequentially fixed in double strength fixative for 30 minutes. Fixed cells were coated with 1% gelatin, scraped and the cell pellet repeatedly washed.

Next, cell pellets were fixed in 2% osmium (1 hr), rinsed with dH$_2$O, and subsequently dehydrated using an ethanol series (50-100%) and embedded in Epon. Ultrathin sections of 70 nm were examined on a JEOL120CX TE microscope.

Confocal Laser scanning microscopy. Following incubation with fluorescently labeled SPMNPs, cells were washed in PBS−/−, fixed with 4% paraformaldehyde, and mounted in Moviol. Fluorescence was captured on confocal microscope (Radiance 2100, Zeiss) connected to an upright Nikon E800 microscope and Image processing was done using Lasersharp 2000 (Zeiss) and Photoshop (Adobe, Calif.).

Fluorescent modified lipid-SPMNPs were developed to confirm the WB results on the Pulse-Chase method using confocal analysis. We observed lipid-SPMNPs predominately localized at the plasma membrane even for prolonged chase period. Furthermore, by using TEM analysis on MEFs incubated with SPMNPs at 4° C. for 20 minutes, we could observe SPMNPs localized exclusively at the cell surface. Based on the fluorescence and TEM analysis results, we designed a detergent- and conjugation-free SPMNP based approach to isolate plasma membrane fractions with a high purity and yield (Method section). We validated the method by studying the level of enrichment and purity of our plasma membrane fractions by WB analysis of an extensive number of compartment specific marker proteins. Our isolated plasma membrane fraction is of high purity and could be further enriched by combining high salt/high pH washes resulting in less than 2%—ER/Golgi contaminations. Similar quality of plasma membrane fractions was isolated from other cell lines like wildtype, PSEN deficient and rescued (PSEN1r) mouse embryonic fibroblasts (MEF).

Figure 1A:
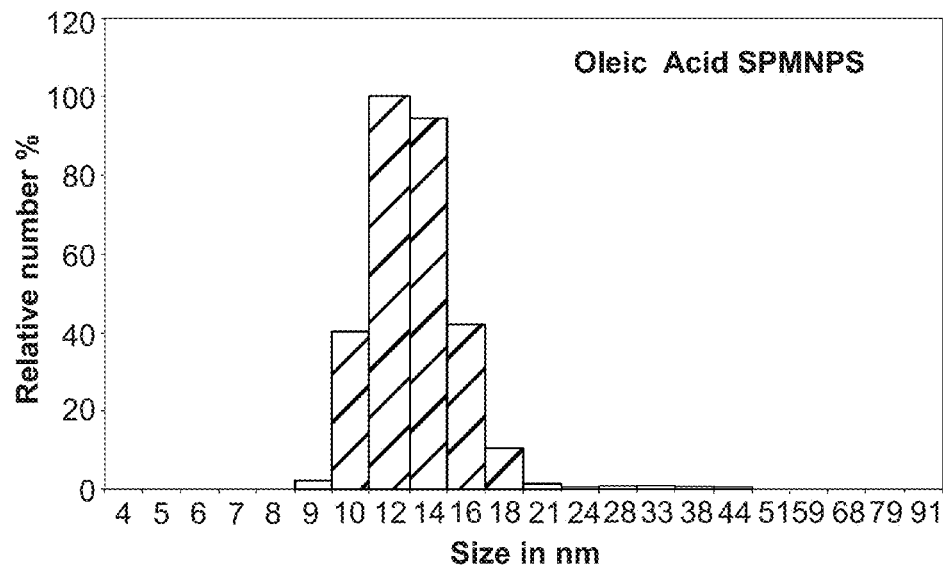
FIG. 1: DLS Size measurement in Relative number (%)
a) SPMNPs in Hexane, b) DMSA-SPMNPs in H$_2$O, c) Amino-Lipid-SPMNPs in H$_2$O, 1d) COOH-Lipid-SPMNPs in H$_2$O, 1e) PEG-Lipid-SPMNPs in H$_2$O, 1f) TMAOH-SPMNPs in H$_2$O, 1(g) COO-TMACl-SPMNPs in H$_2$O, 1(h) SPMNPs in Medium DMEM/F12. These measurements illustrate the monodisperse character of the nanoparticles. The most abundant fraction is presented as 100%.
1(i) UV-Vis measurement of SPMNPs in medium at 1000 nm for 4 hours indicates the stability of the nanoparticles in medium, 1(j) Trypan blue based cell viability test in HeLa Cells for 2 hours SPMNPs incubation, indicates that there is no toxic effect of any of the surface coatings. 1(k) shows exemplary illustrations of the various coated particles referenced in FIGS. 1(a)-1(j).
Figure 1B:
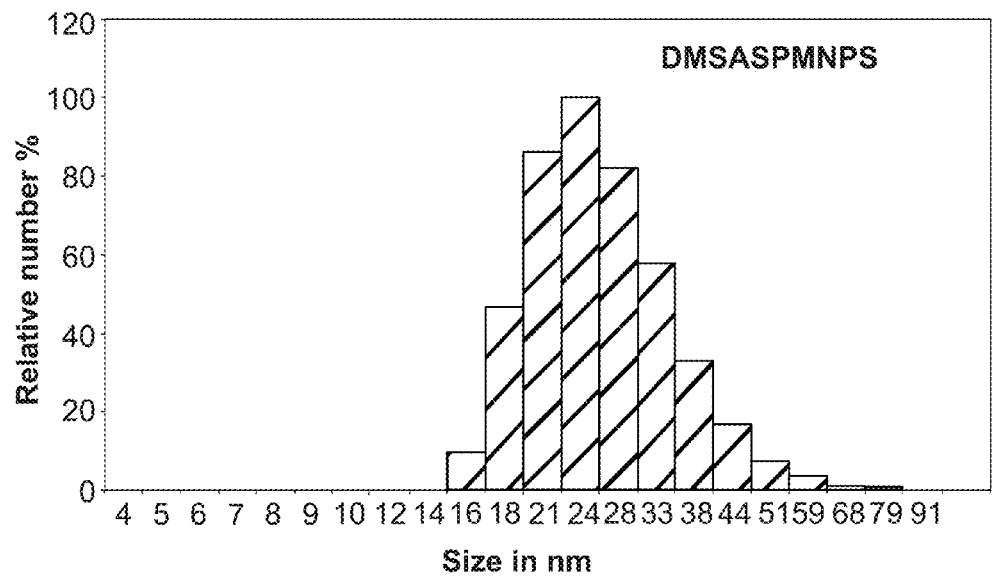
Figure 1C:
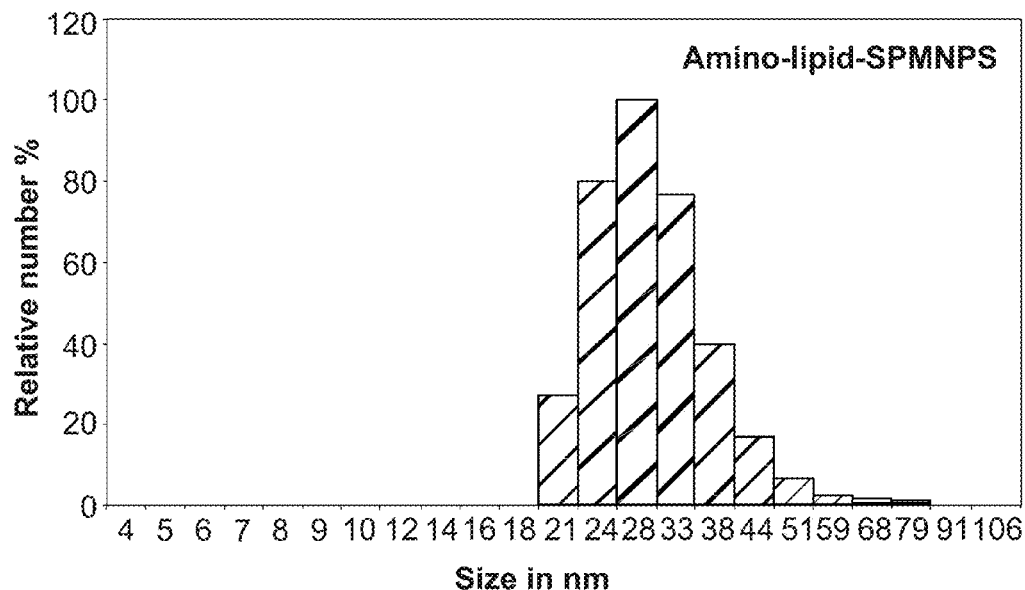
Figure 1D:
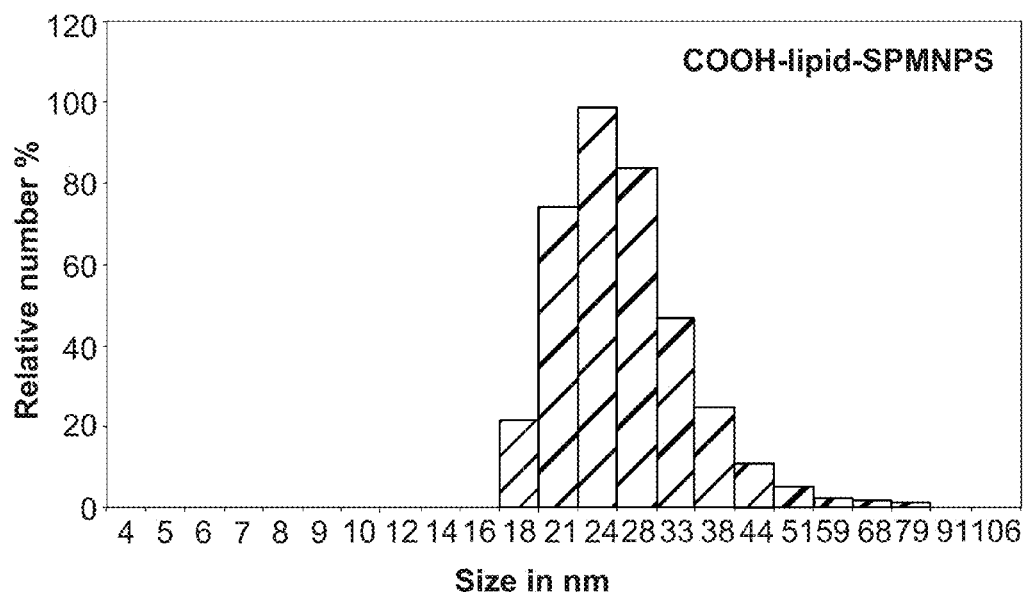
Figure 1E:
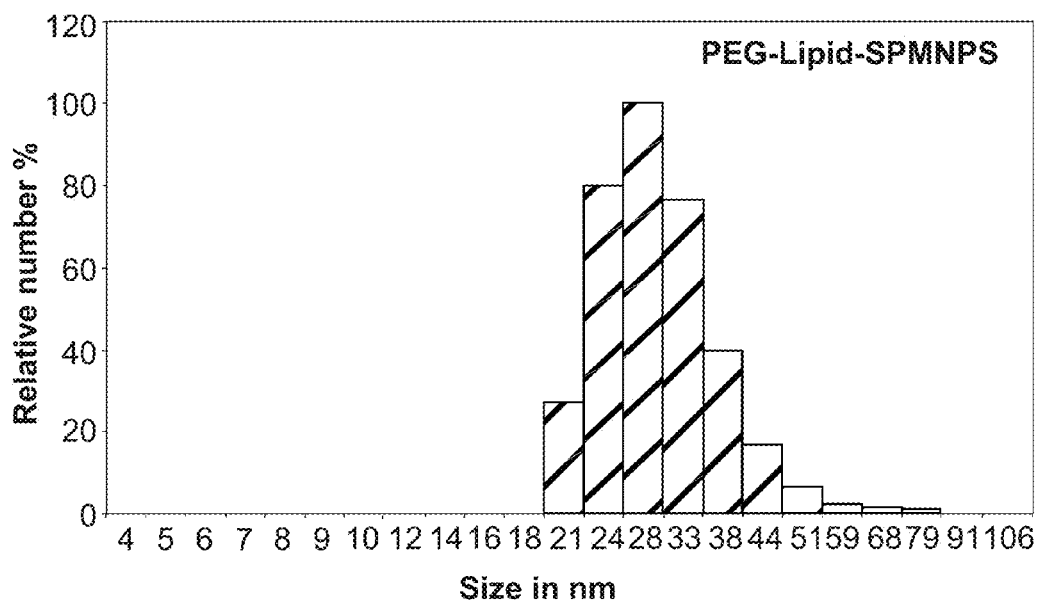
Figure 1F:
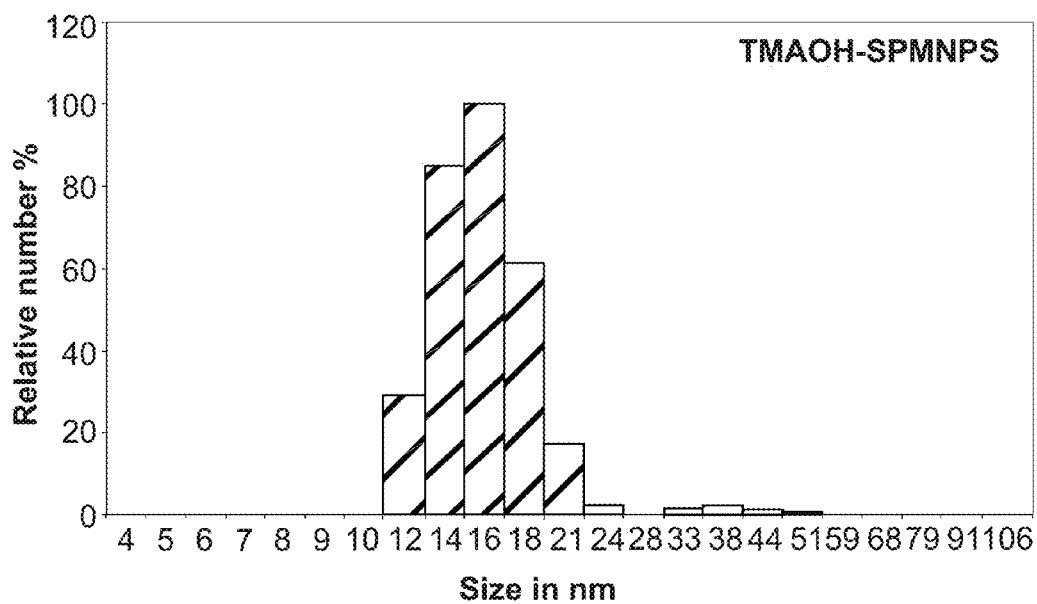
Figure 1G:
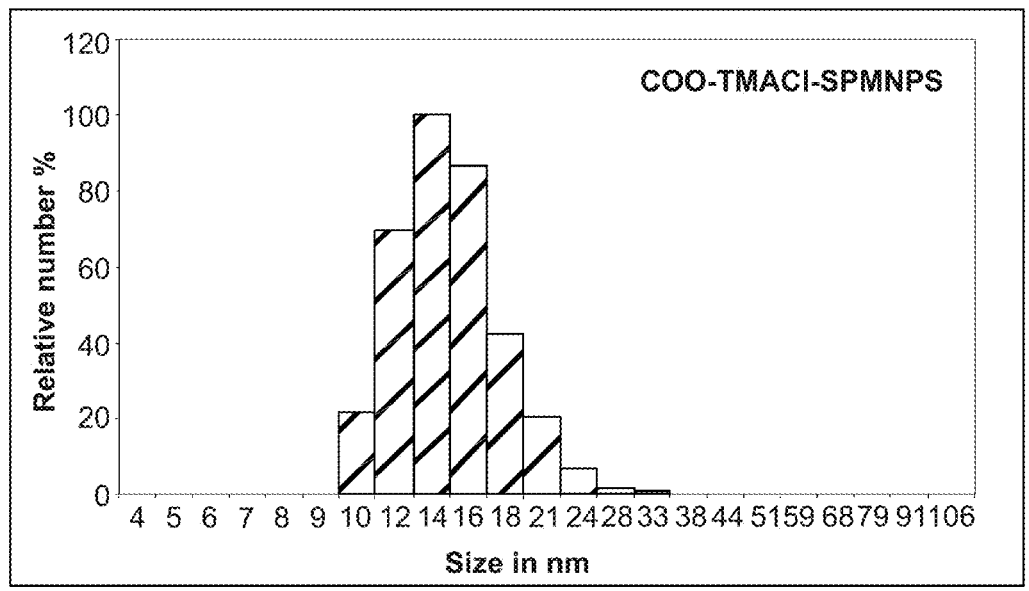
Figure 1H:
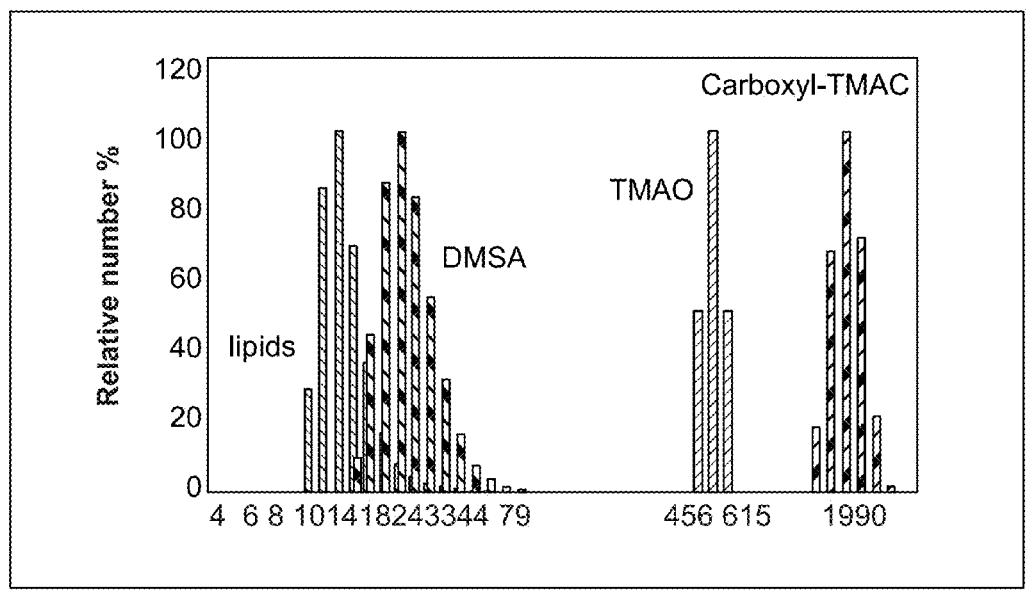
Figure 1I:
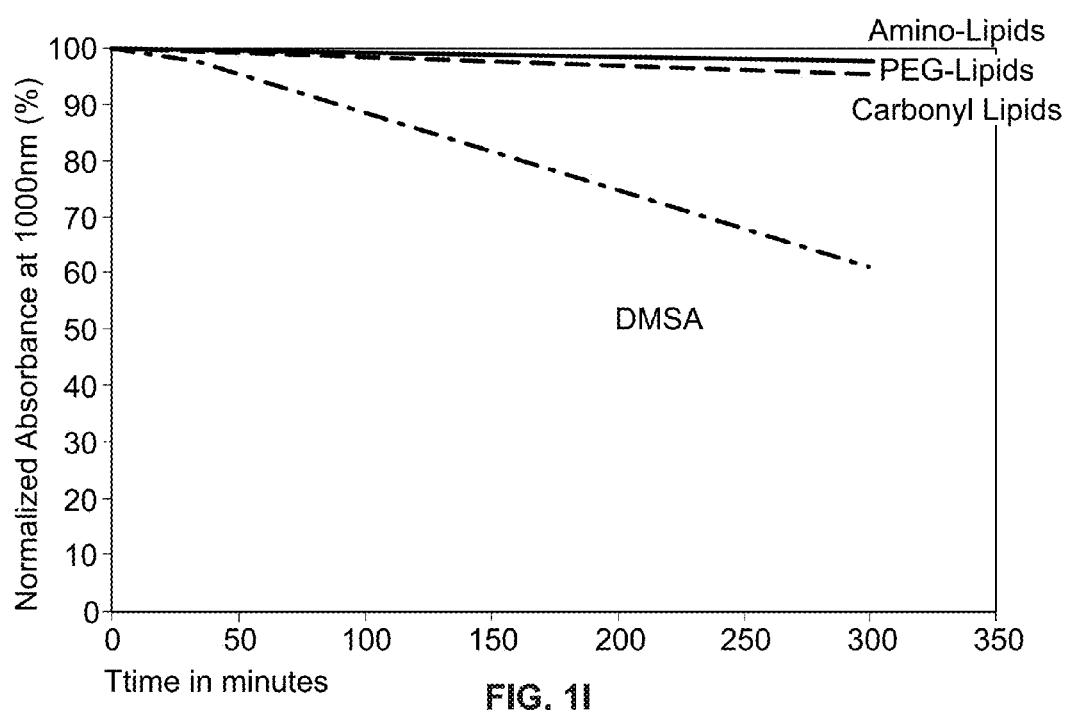
Figure 1J:
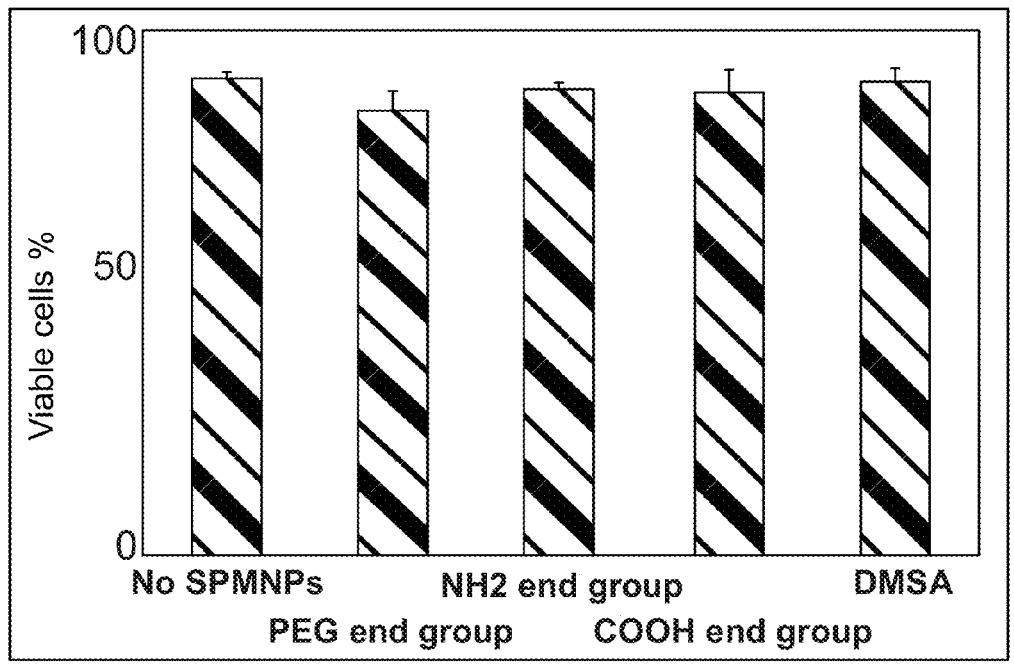
Figure 1K:
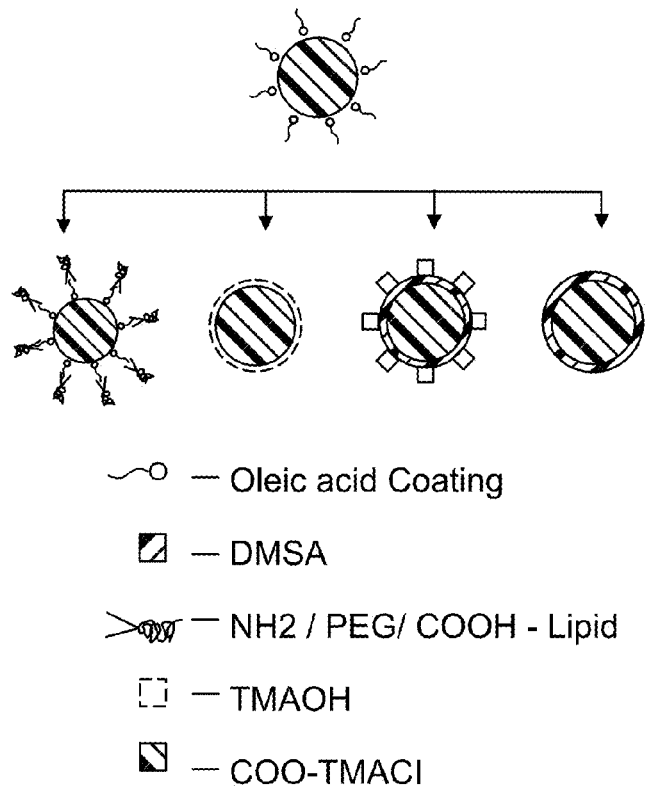
Figure 2:
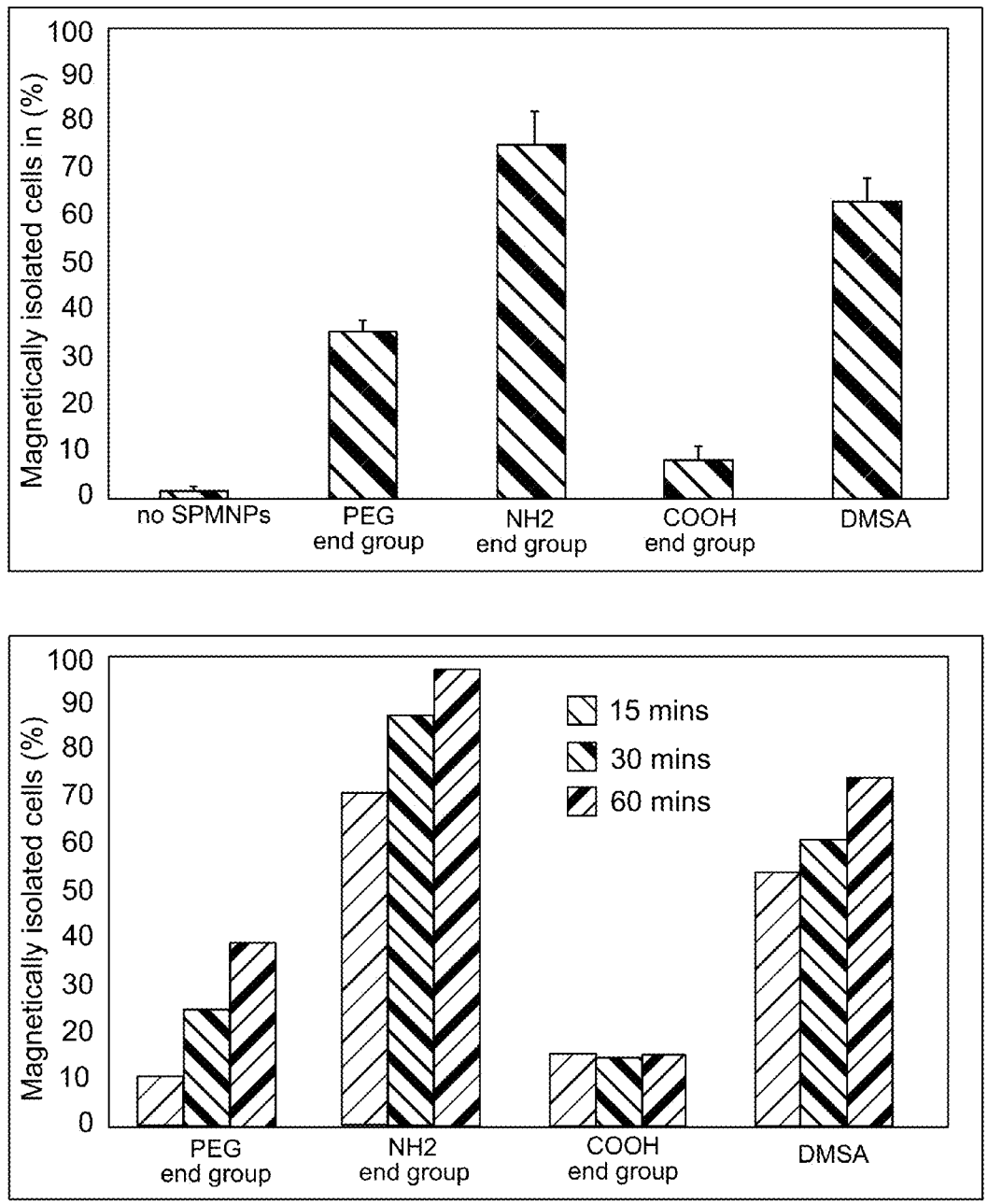
FIG. 2: (top) Magnetically Tagged HeLa Cells (% labelled cells of total cell amount). After 2 hours of SPMNPs incubation in medium at 37° C. These data show that the hydrophobic nature of the nanoparticle coating has an effect on the labelling of specific cell types.
(bottom) Sequential incubation of SPMNPs (100 µg/ml) in HeLa Cells for increasing time period 15, 30, and 60 minutes.
Figure 3A:
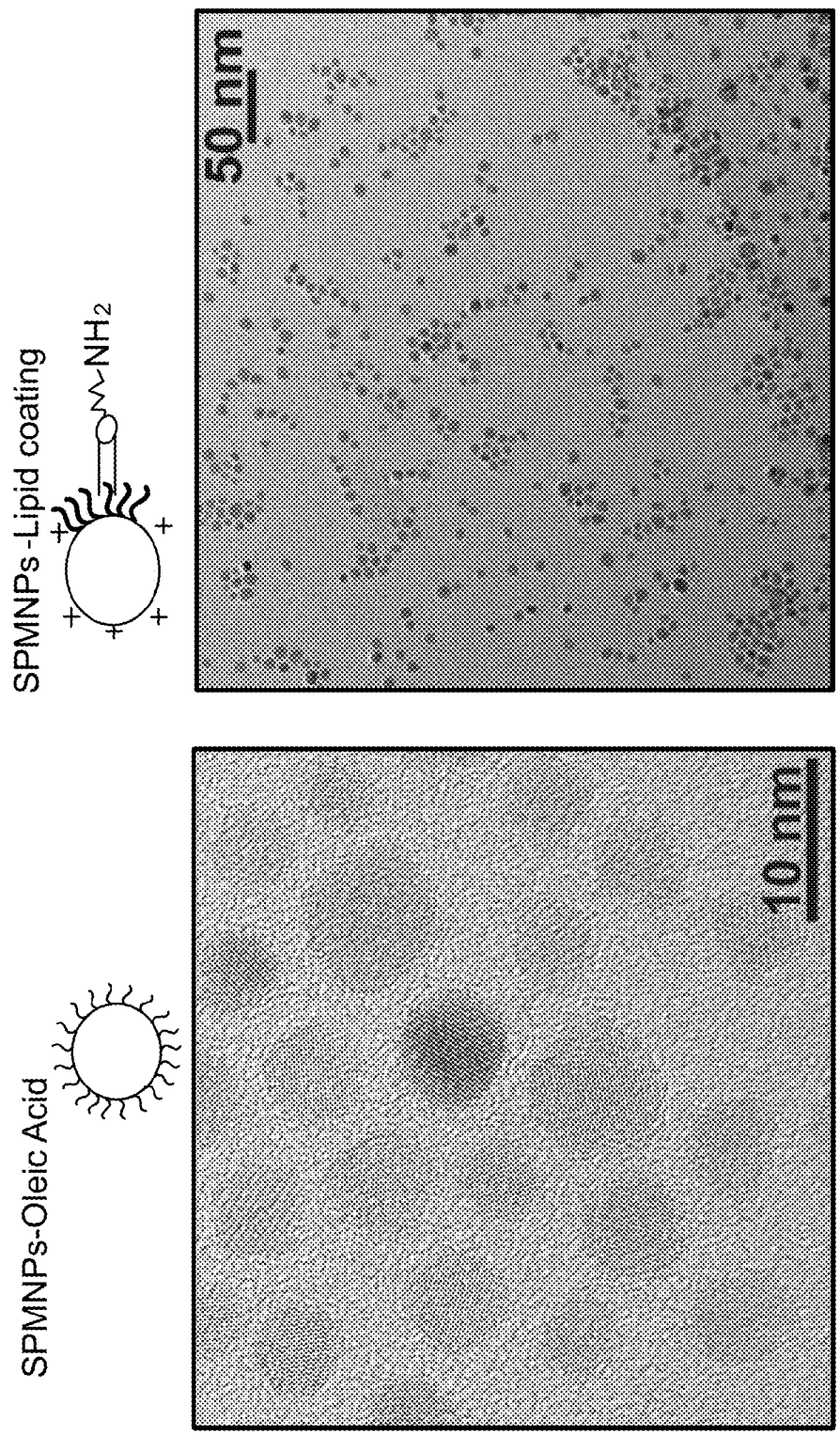
FIG. 3: Nanoparticle Synthesis and Characterization. A) Transmission Electron Microscope images of Fe$_3$O$_4$ nanoparticles coated with oleic acid (left side) and coated with lipids (right side). B) Dynamic Light Scattering (DLS) graphs of Fe$_3$O$_4$ nanoparticles coated with oleic acid (top) and coated with amino end-group lipids (bottom), illustrating the monodisperse nature of the nanoparticle population. The most abundant fraction is presented as 100%. C) Magnetic properties measurement by alternating gradient field magnetometer (AGFM)—Oleic Acid coated (Dark line) and Lipid coated Fe$_3$O$_4$ nanoparticles (dotted line) where X-axis is magnetic field (KOe) and Y-axis is magnetization (emu/g nanoparticles). The data illustrate the superparamagnetic properties of the nanoparticles, D) Zeta Potential measurement on amino end-group lipid coated Fe$_3$O$_4$ nanoparticles for different pH range (2-11) shows that the nanoparticles are nanoparticle are positively charged and suitable for the plasma membrane isolation.
Figure 3B:
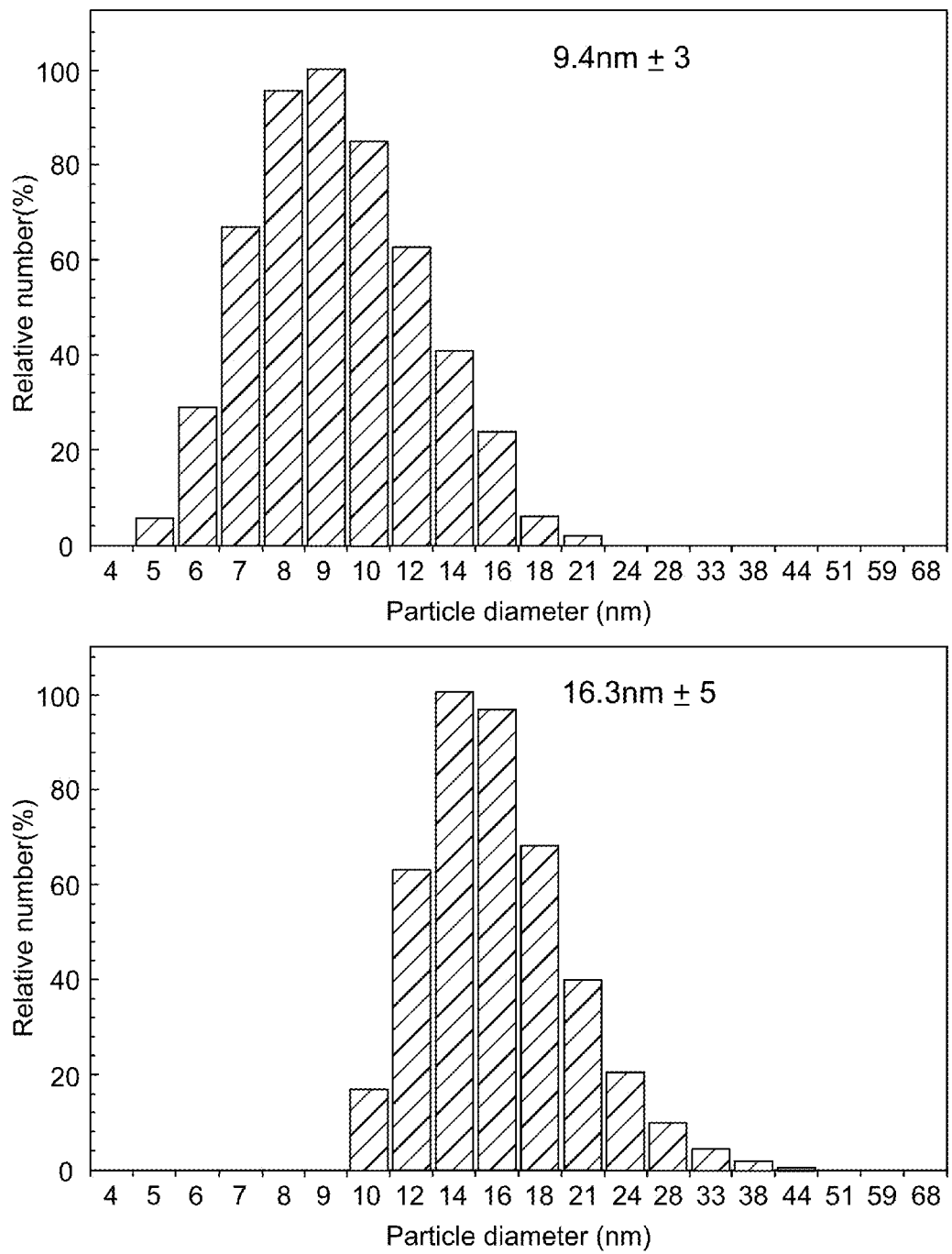
Figure 3C:
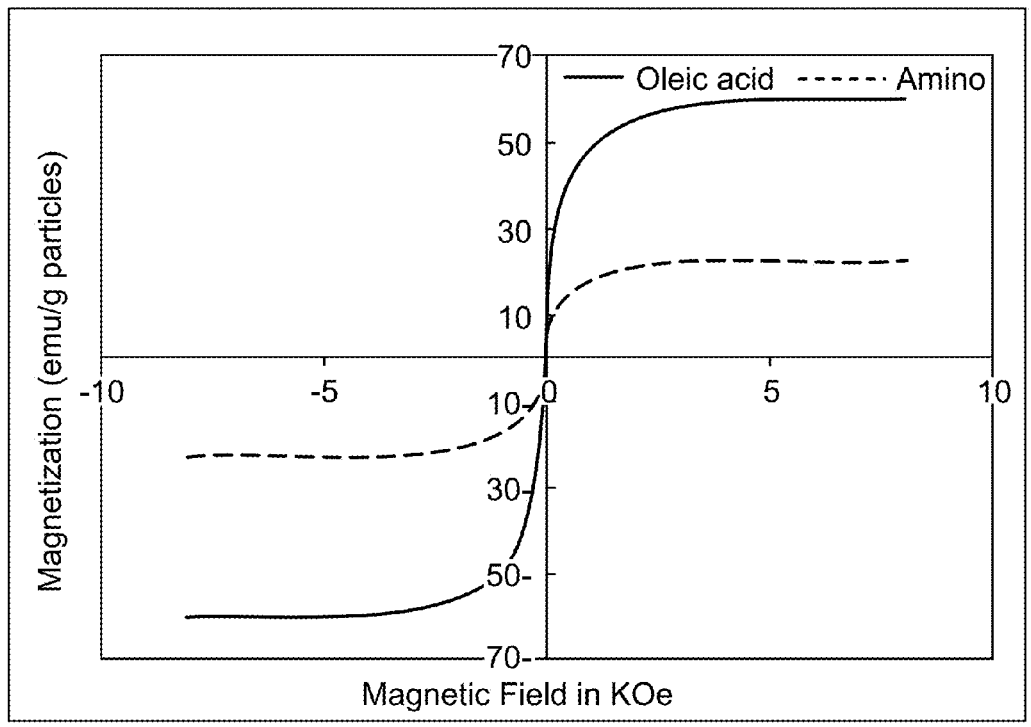
Figure 3D:
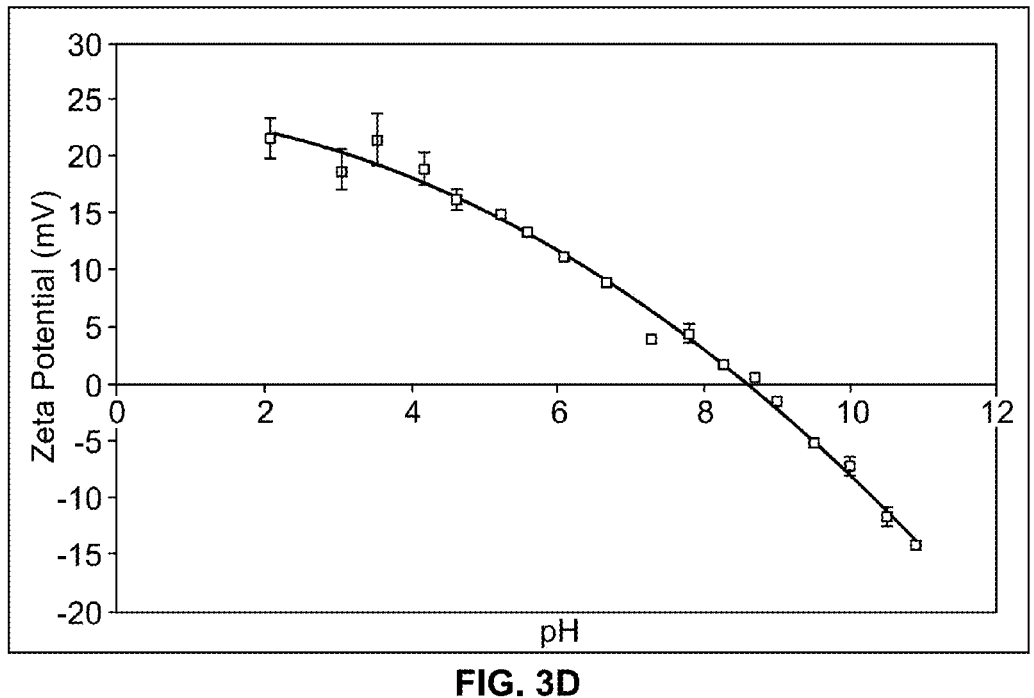
Figure 4A:
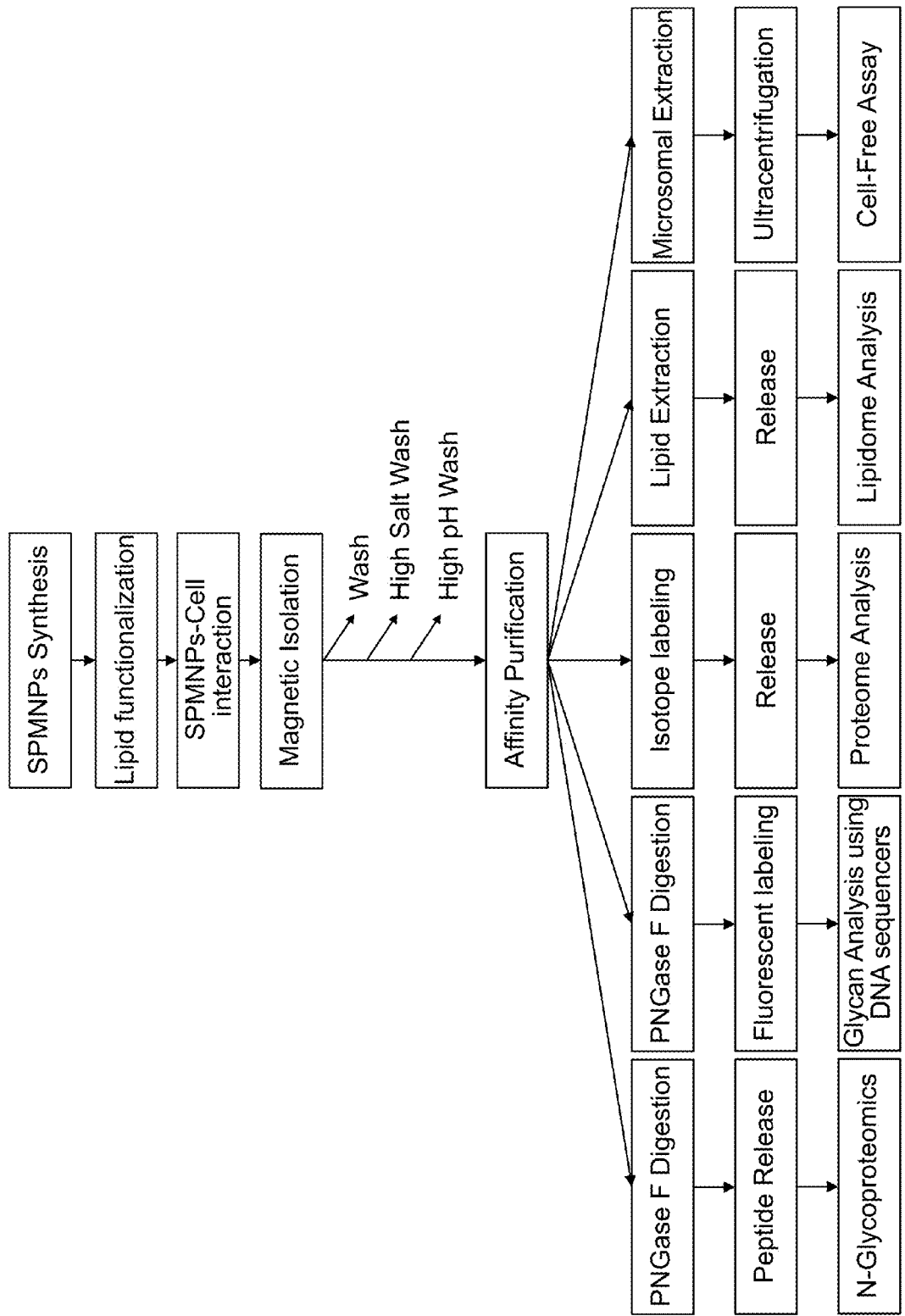
FIG. 4: Plasma membrane Omics Analysis. A) Step flow diagram SPMNPs based plasma membrane isolation and different omics analysis. B Schematic representation of SPMNPs-Cell interaction and magnetic plasm membrane isolation.
Figure 4B:
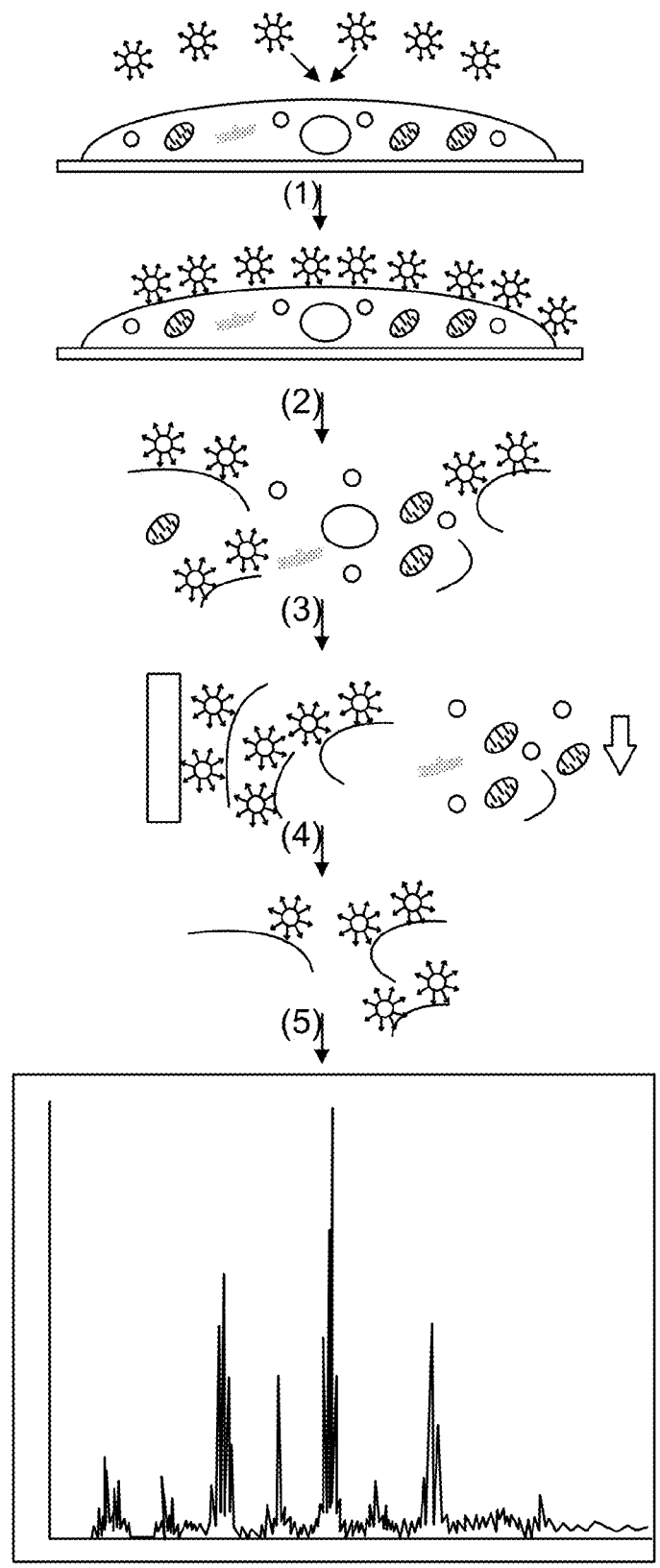
Figure 5A:
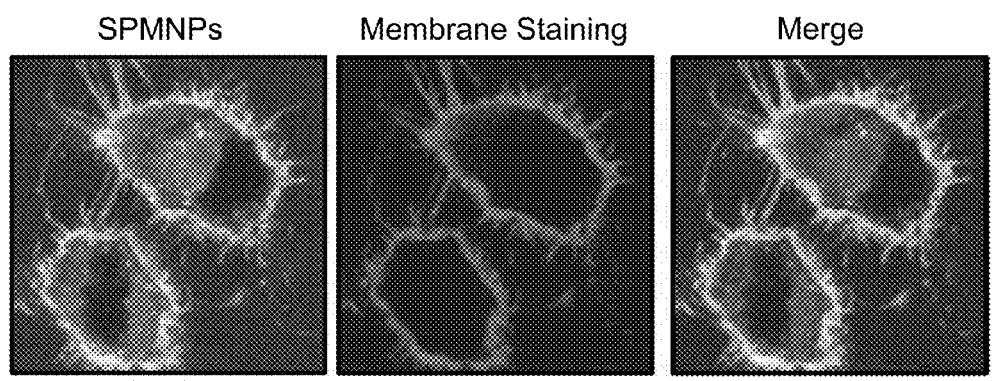
FIG. 5: SPMNPs—localize to the cell surface of MEFs cells. A) Confocal laser scanning microscopy images of MEFs Wt incubated with fluorescent modified SPMNPs for Pulse period of 15 minutes at 37° C. The data show that the SPMNPs co-localize with a validated membrane marker.
B) Transmission electron microscopy images at different resolution of MEFs wt cell membranes incubated SPMNPs for a pulse period of 15 minutes at 4° C.
C) Western blot analysis of various proteins with appropriate primary and secondary antibodies. Protein sample was resolved in a 4-12% SDS-Page gradient gel in each lane. Lane 1-3 represents Post Nuclear Supernatant (PNS), fraction which is unbound to the membrane(UB) and fraction which is bound to the membrane (B).
List of marker proteins and corresponding organelle marker used: Na$^+$K$^+$ATPase—Plasma Membrane, Lamin A—Nucleus, GM130-Golgi Apparatus, GADPH-Cytosol, RER1p, BIP & RBI—Endoplasmic Reticulum, Actin—Cytoskeleton, GM130 for Golgi compartments, Rab 7—Late Endosomes, HSP60-Mitochondria, P58-Intermediate Compartments. D) Western blot protein signal intensity quantification—Y-axis represent—total percentage retainment of protein in Bound fraction with respect to PNS and X-axis represents organelle marker proteins. E) glycoprotein specific Ponceau staining of PNS, UB and B fraction of MEFs Wildtype and MEFs PSDKO. F) Gamma-Secretase Cell free activity Assay on PNS and Plasma Membrane fraction and Intensity quantification of total AICD level and enrichment with respect to PNS.
Figure 5B:
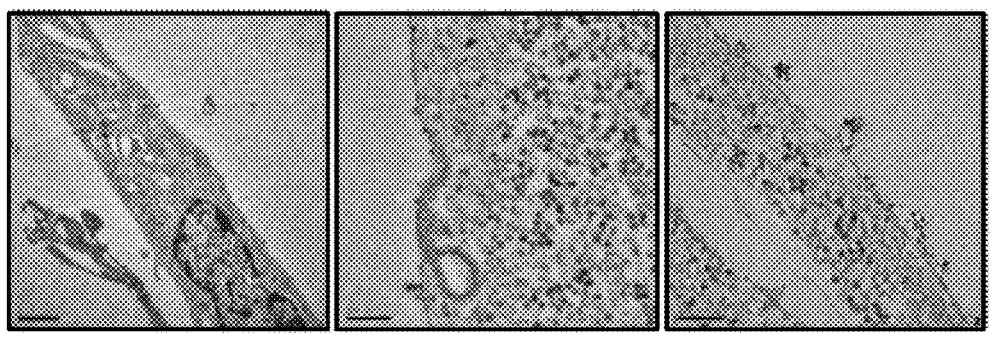
Figure 5C:
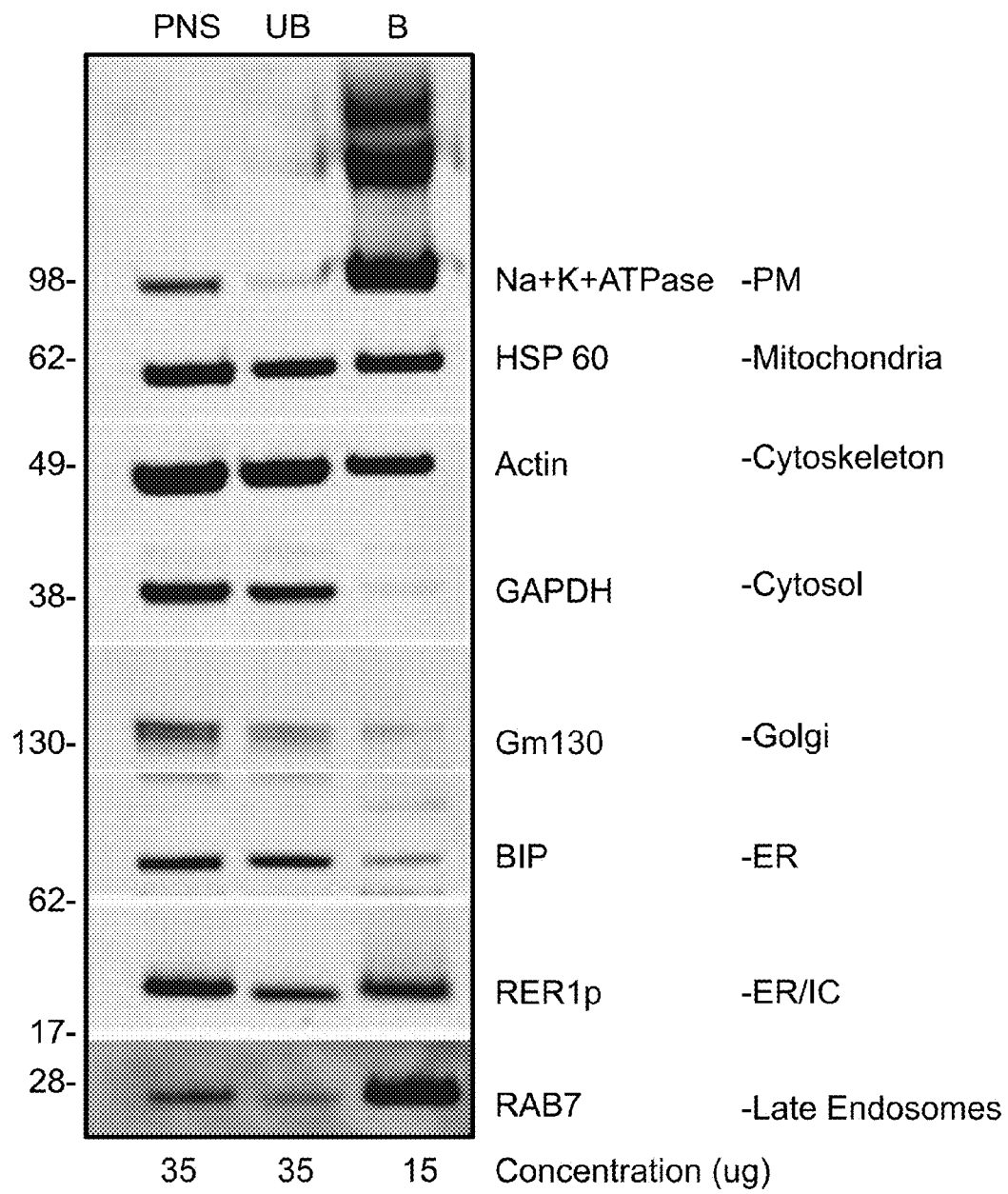
Figure 5D:
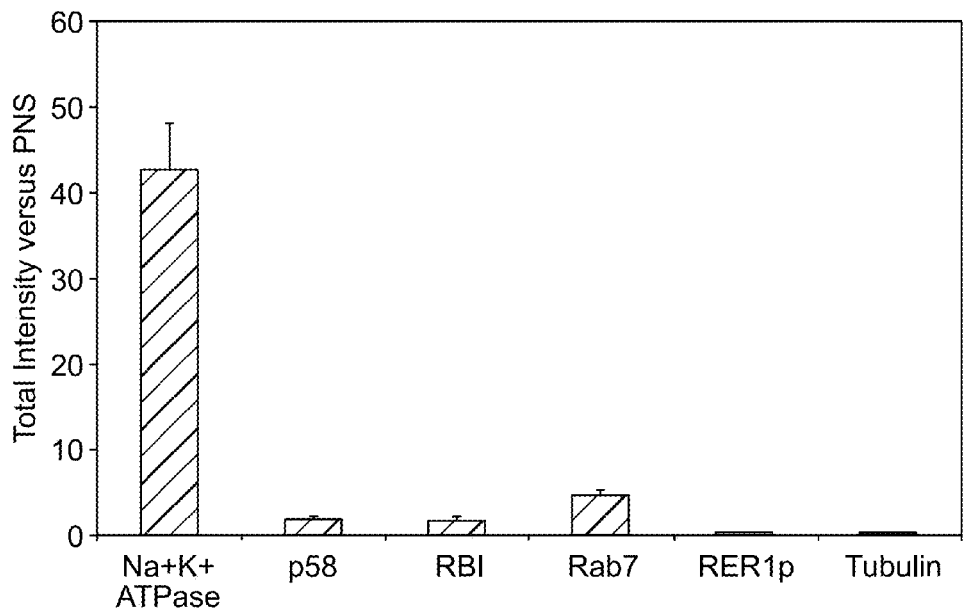
Figure 5F:
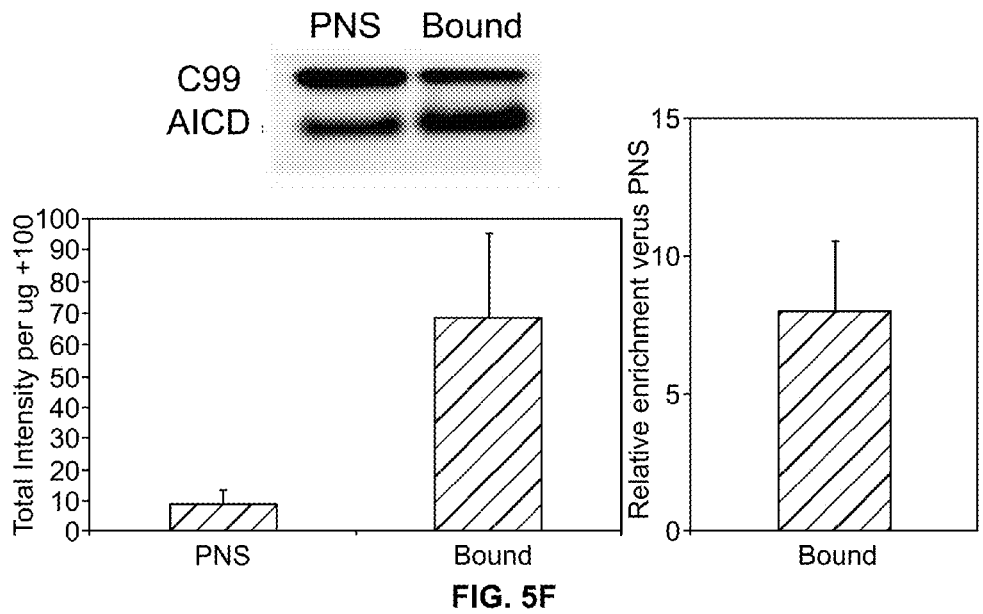
Figure 5E:
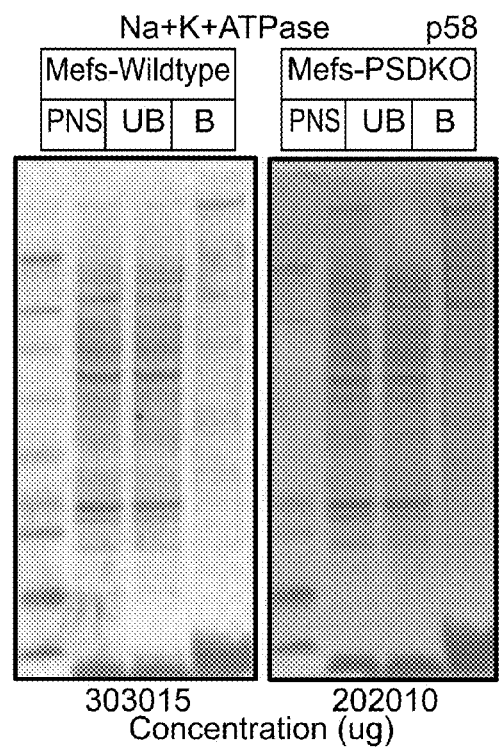
Figure 6:
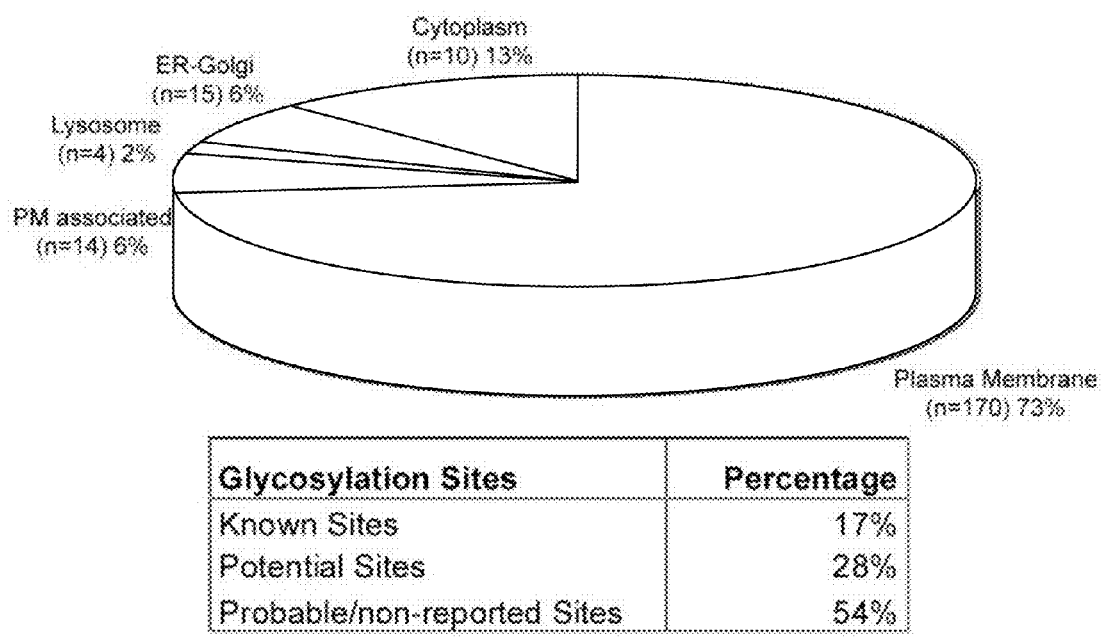
FIG. 6: N-Glycoproteomics analysis on MEFs Wt plasma membrane fraction. Identification of the glycoproteins in the PM shows that about 75% of the identified proteins are plasma membrane derived.
Figure 7:
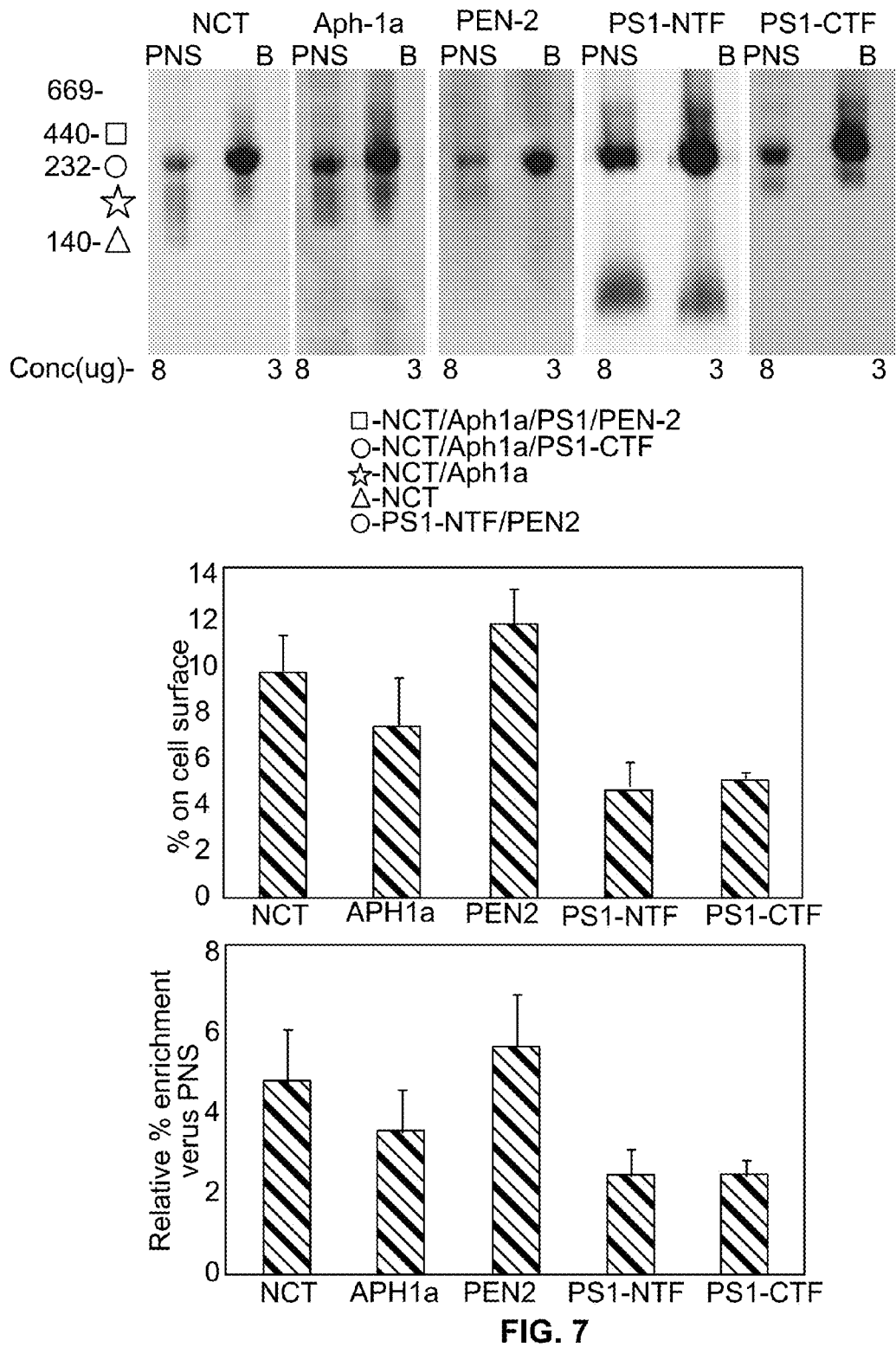
FIG. 7: Blue-Native Gel based gamma-secretase complex isolation: a) Levels of gamma-secretase components (NCT, APh-1a, PEN-2, PSEN$^1$-NTF, PSEN1-CTF) at the plasma membrane relative to PNS fractions, showing a significant enrichment of the gamma secretase components in the PM; b) percentage of full gamma-secretase complexes at the plasma membrane relative to PNS and % enrichment at the plasma membrane versus PNS.
Figure 8:
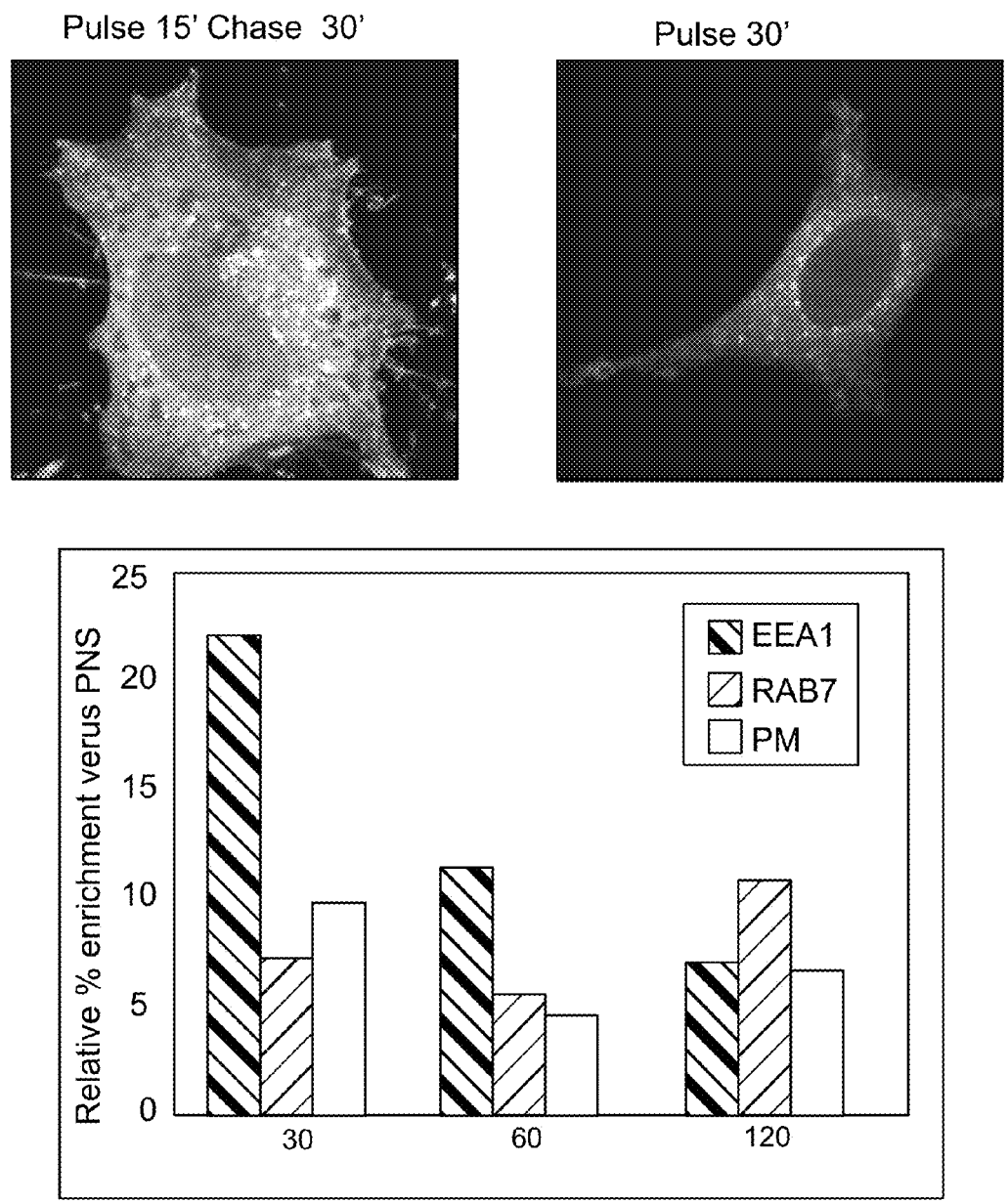
FIG. 8: DMSA-SPMNPs based Endosomal Compartmental isolation: a) Confocal laser scanning microscopy images of HeLa incubated with fluorescent modified DMSA-SPMNPs for Pulse period of 15 minutes & Chase 30 minutes at 37° C. and Pulse period of 30 minutes at 37° C. b) Western blot protein signal intensity quantification—Y-axis represent—Relative enrichment versus PNS and X-axis represent Chase time incubation for 30, 60 and 120 minutes. List of marker proteins and corresponding organelle marker used: Na$^+$K$^+$ATPase—Plasma Membrane, EEA1—Early Endosomes and RAB7—Late Endosomes.
Figure 9:
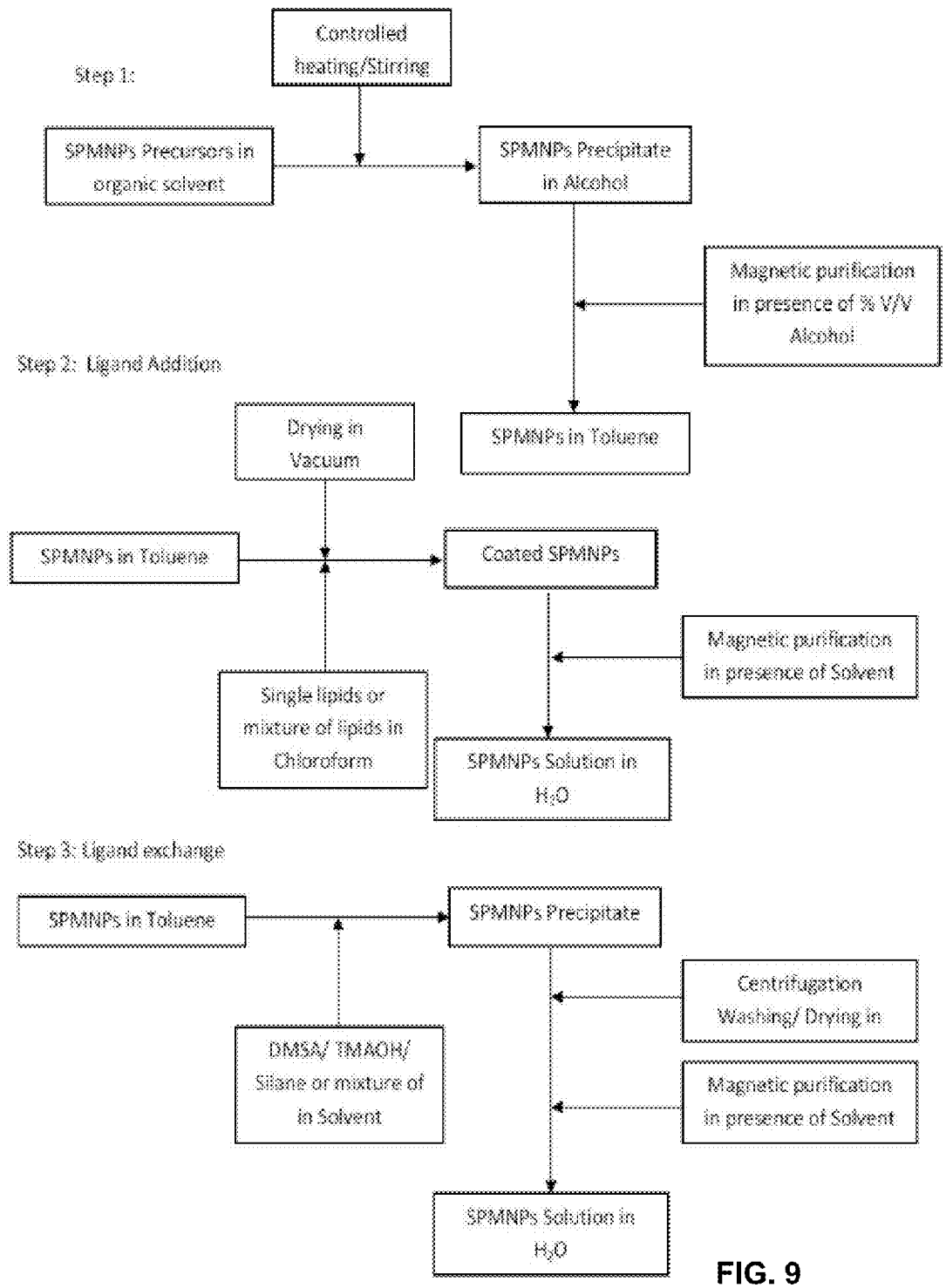
FIG. 9 shows a schematic overview of the manufacture of magnetic nanoparticles in accordance with certain embodiments of the invention.

The invention claimed is:

1. An isolated complex of a positively charged nanoparticle with a plasma membrane or an endosome, each isolated from other cellular organelles, wherein the positively charged nanoparticle comprises
a magnetic nanoparticle coated with a layer of hydrophilic end groups, wherein
the coated nanoparticle has a zeta potential in the range of 10-30 mV at pH 7 and a diameter between 1 and 100 nm, and
the hydrophilic end groups comprise
an inner layer consisting essentially of saturated and/or monounsaturated fatty acids bound to said nanoparticle and
an outer layer of phospholipids bound to the fatty acids and conjugated to monomethoxy polyethyleneglycol (PEG),
and wherein said nanoparticle does not comprise a peptide moiety.

2. The isolated complex according to claim 1, wherein said hydrophilic end groups comprise one or more moieties selected from the group consisting of a phosphonate, an amine, azido, epoxy, —NH$_2$, —COOH, unsubstituted or substituted PEG, PDP ((2-pyridyldithio)propionate), —CHO, and —SH.

3. The isolated complex according to claim 1, wherein the conjugated phospholipids in the outer layer are selected from the group consisting of 1,2-distearoyl-sn-glycero-3-phosphoethanolamine-N[carboxy(polyethylene glycol)-2000] (DSPE-PEG-COOH), 1,2-distearoyl-sn-glycero-3-phosphoethanolamine-N-[Amino (polyethylene glycol)-2000] (DSPE-PEG-Amine), 1,2-distearoyl-sn-glycero-3-phosphoethanolamine-N-[methoxy(polyethylene glycol)-2000] (DSPE-PEG), DSPE-PEG(2000) Maleimide and DSPE-PEG (2000) Carboxyfluroscein.

4. A method for isolating a plasma membrane of a cell, a fraction thereof, or a plasma membrane derived organelle, comprising:
a) providing a population of intact and suspended cells at a temperature where endocytic uptake by a cell is inhibited,
b) contacting said intact cells with positively charged magnetic nanoparticles, thereby allowing the binding of magnetic nanoparticles to and into the cell plasma membrane, wherein the positively charged nanoparticle comprises a magnetic nanoparticle coated with a layer of hydrophilic end groups, wherein
the coated nanoparticle has a zeta potential in the range of 10-30 mV at pH 7 and a diameter between 1 and 100 nm, and
the hydrophilic end groups comprise
an inner layer consisting of saturated and/or monounsaturated fatty acids bound to said nanoparticle and
an outer layer of phospholipids bound to the fatty acids and conjugated to monomethoxy polyethyleneglycol (PEG),
and wherein said nanoparticle does not comprise a peptide moiety,
c) removing unbound magnetic nanoparticles,
d) disrupting the cells,
e) removing cellular organelles,
f) isolating from the disrupted cells by magnetic attraction the plasma membranes with magnetic nanoparticles.

5. The method according to claim 4, wherein said hydrophilic end groups comprise one or more moieties selected from the group consisting of a phosphonate, an amine, azido, epoxy, —NH$_2$, —COOH, unsubstituted or substituted PEG, PDP ((2-pyridyldithio)propionate), —CHO, and —SH.

6. The method according to claim 4, wherein the conjugated phospholipids in the outer layer are selected from the group consisting of 1,2-distearoyl-sn-glycero-3-phosphoethanolamine-N[carboxy(polyethylene glycol)-2000](DSPE-PEG-COOH), 1,2-distearoyl-sn-glycero-3-phosphoethanolamine-N-[Amino (polyethylene glycol)-2000] (DSPE-PEG-Amine), 1,2-distearoyl-sn-glycero-3-phosphoethanolamine-N-[methoxy(polyethylene glycol)-2000] (DSPE-PEG), DSPE-PEG(2000) Maleimide and DSPE-PEG(2000) Carboxyfluroscein.

7. A method for isolating a plasma membrane of a cell, a fraction thereof, or a plasma membrane derived organelle, comprising:
a) providing a population of intact and suspended cells at a temperature where endocytic uptake by a cell is inhibited,
b) contacting said intact cells with positively charged magnetic nanoparticles, thereby allowing the binding of magnetic nanoparticles to and into the cell plasma membrane, wherein the positively charged nanoparticle comprises a magnetic nanoparticle coated with a layer of hydrophilic end groups, wherein
the coated nanoparticle has a zeta potential in the range of 10-30 mV at pH 7 and a diameter between 1 and 100 nm, and
the layer of hydrophilic end groups comprise hydrophilic layer covalently bound to the nanoparticles,
and wherein said nanoparticle does not comprise a peptide moiety,
c) removing unbound magnetic nanoparticles,
d) disrupting the cells,
e) removing cellular organelles,
f) isolating from the disrupted cells by magnetic attraction the plasma membranes with magnetic nanoparticles.

8. The method according to claim 7, wherein the covalently bound hydrophilic layer is silane, dimercaptosuccinic acid (DMSA) or ammonium chloride.

9. An isolated complex of a positively charged nanoparticle with a plasma membrane or an endosome, each isolated from other cellular organelles, wherein the positively charged nanoparticle comprises
a magnetic nanoparticle coated with a layer of hydrophilic end groups, wherein
the coated nanoparticle has a zeta potential in the range of 10-30 mV at pH 7 and a diameter between 1 and 100 nm, and
the hydrophilic end groups comprise a hydrophilic layer covalently bound to the nanoparticles,
and wherein said nanoparticle does not comprise a peptide moiety.

10. The isolated complex according to claim 9, wherein the covalently bound hydrophilic layer is silane, dimercaptosuccinic acid (DMSA) or ammonium chloride.

* * * * *